(12) United States Patent
Hirose et al.

(10) Patent No.: US 11,980,416 B2
(45) Date of Patent: May 14, 2024

(54) OPHTHALMOLOGIC INFORMATION PROCESSING APPARATUS, OPHTHALMOLOGIC APPARATUS, OPHTHALMOLOGIC INFORMATION PROCESSING METHOD, AND RECORDING MEDIUM

(71) Applicant: TOPCON CORPORATION, Tokyo (JP)

(72) Inventors: Ryoichi Hirose, Tokyo (JP); Tatsuo Yamaguchi, Warabi (JP)

(73) Assignee: TOPCON CORPORATION, Tokyo (JP)

( * ) Notice: Subject to any disclaimer, the term of this patent is extended or adjusted under 35 U.S.C. 154(b) by 764 days.

(21) Appl. No.: 17/083,312

(22) Filed: Oct. 29, 2020

(65) Prior Publication Data

US 2021/0038068 A1    Feb. 11, 2021

Related U.S. Application Data

(63) Continuation of application No. PCT/JP2019/051169, filed on Dec. 26, 2019.

(30) Foreign Application Priority Data

Jan. 28, 2019  (JP) .................................. 2019-012330

(51) Int. Cl.
*A61B 3/00*  (2006.01)
*A61B 3/10*  (2006.01)

(52) U.S. Cl.
CPC .......... *A61B 3/0025* (2013.01); *A61B 3/1005* (2013.01); *A61B 3/102* (2013.01)

(58) Field of Classification Search
CPC ...... A61B 3/0025; A61B 3/1005; A61B 3/102
See application file for complete search history.

(56) References Cited

U.S. PATENT DOCUMENTS

| 2011/0199579 A1 | 8/2011 | Muto |
| 2012/0063660 A1 | 3/2012 | Imamura et al. |

(Continued)

FOREIGN PATENT DOCUMENTS

| JP | 2010-279440 A | 12/2010 |
| JP | 2011-167285 A | 9/2011 |

(Continued)

OTHER PUBLICATIONS

International Search Report and Written Opinion dated Mar. 10, 2020 for PCT/JP2019/051169 filed on Dec. 26, 2019, 8 pages including English Translation of the International Search Report.

(Continued)

*Primary Examiner* — James C. Jones
(74) *Attorney, Agent, or Firm* — XSENSUS LLP

(57) ABSTRACT

An ophthalmologic information processing apparatus corrects an image of a subject's eye formed by arranging a plurality of A-scan images acquired by scanning inside the subject's eye with measurement light deflected around a scan center position. The ophthalmologic information processing apparatus includes a specifying unit and a transforming unit. The specifying unit is configured to specify a transformation position along a traveling direction of the measurement light passing through the scan center position, the transformation position corresponding to a pixel position in the image. The transforming unit is configured to transform the pixel position into the transformation position.

17 Claims, 13 Drawing Sheets

(56) References Cited

U.S. PATENT DOCUMENTS

| | | |
|---|---|---|
| 2012/0188510 A1 | 7/2012 | Suehira et al. |
| 2012/0189184 A1 | 7/2012 | Matsumoto et al. |
| 2015/0182111 A1 | 7/2015 | Namiki et al. |
| 2018/0289257 A1* | 10/2018 | Ikegami ............... A61B 3/1225 |
| 2020/0138283 A1 | 5/2020 | Yamaguchi et al. |

FOREIGN PATENT DOCUMENTS

| | | |
|---|---|---|
| JP | 2012-147977 A | 8/2012 |
| JP | 2012-148003 A | 8/2012 |
| JP | 2015-102537 A | 6/2015 |
| JP | 2015-104582 A | 6/2015 |
| JP | 2018-020192 A | 2/2018 |
| JP | 2018-175258 A | 11/2018 |
| WO | 2019/008968 A1 | 1/2019 |

OTHER PUBLICATIONS

Office Action dated Apr. 25, 2023, in corresponding Japanese patent Application No. 2022-124968, 4 pages.
Office Action dated Jul. 26, 2022 in Japanese Patent Application No. 2019-012330, 6 pages.
Extended European Search Report dated Sep. 5, 2022 in European Patent Application No. 19912859.6, 7 pages.

* cited by examiner

OPHTHALMOLOGIC INFORMATION PROCESSING APPARATUS, OPHTHALMOLOGIC APPARATUS, OPHTHALMOLOGIC INFORMATION PROCESSING METHOD, AND RECORDING MEDIUM

CROSS-REFERENCE TO RELATED APPLICATIONS

The present application is a continuation application of International Patent Application No. PCT/JP2019/051169, filed Dec. 26, 2019, which claims priority to Japanese Patent Application No. 2019-012330, filed Jan. 28, 2019. The contents of these applications are incorporated herein by reference in their entirety.

FIELD

The disclosure relates to an ophthalmologic information processing apparatus, an ophthalmologic apparatus, an ophthalmologic information processing method, and a recording medium.

BACKGROUND

In recent years, attention has been drawn to optical coherence tomography (OCT) which is used to form images representing the surface morphology and the internal morphology of an object using light beams emitted from a laser light source or the like. Since OCT does not have invasiveness to human body as X-ray CT (Computed Tomography) does, development of application of OCT in medical field and biology field is particularly expected. For example, in the ophthalmologic field, apparatuses for forming images of the fundus, the cornea, or the like have been in practical use. Such an apparatus using OCT imaging (OCT apparatus) can be used to observe a variety of sites of a subject's eye. In addition, because of the ability to acquire high precision images, the OCT apparatus is applied to the diagnosis of various eye diseases.

In case of performing OCT measurement on a predetermined site inside the subject's eye, the measurement light for scanning the predetermined site is made incident on the eye from the pupil, and the measurement light is deflected, for example, around the scan center position arranged near the pupil. For example, an A-scan image is formed from acquired A-scan data, and a tomographic image (B-scan image) is obtained by arranging a plurality of A-scan images in a B-scan direction (for example, Japanese Unexamined Patent Publication No. 2011-167285).

SUMMARY

One aspect of some embodiments is an ophthalmologic information processing apparatus for correcting an image of a subject's eye formed by arranging a plurality of A-scan images acquired by scanning inside the subject's eye with measurement light deflected around a scan center position. The ophthalmologic information processing apparatus includes: a specifying unit configured to specify a transformation position along a traveling direction of the measurement light passing through the scan center position, the transformation position corresponding to a pixel position in the image; and a transforming unit configured to transform the pixel position into the transformation position specified by the specifying unit.

Another aspect of some embodiments is an ophthalmologic information processing apparatus for correcting two-dimensional or three-dimensional scan data of a subject's eye formed by arranging a plurality of A-scan data acquired by scanning inside the subject's eye with measurement light deflected around a scan center position. The ophthalmologic information processing apparatus includes: a specifying unit configured to specify a transformation position along a traveling direction of the measurement light passing through the scan center position, the transformation position corresponding to a scan position in the scan data; and a transforming unit configured to transform the scan position into the transformation position specified by the specifying unit.

Still another aspect of some embodiments is an ophthalmologic apparatus, including an acquisition unit configured to acquire the plurality of A-scan images or the plurality of A-scan data using optical coherence tomography; and the ophthalmologic information processing apparatus of any one of the above.

Still another aspect of some embodiments is an ophthalmologic information processing method of correcting an image of a subject's eye formed by arranging a plurality of A-scan images acquired by scanning inside the subject's eye with measurement light deflected around a scan center position. The ophthalmologic information processing method includes method includes: a specifying step of specifying a transformation position along a traveling direction of the measurement light passing through the scan center position, the transformation position corresponding to a pixel position in the image; and a transforming step of transforming the pixel position into the transformation position specified in the specifying step.

Still another aspect of some embodiments is a non-transitory computer readable recording medium storing a program of causing a computer to execute each step of the ophthalmologic information processing method of the above.

DETAILED DESCRIPTION

Figure 1:
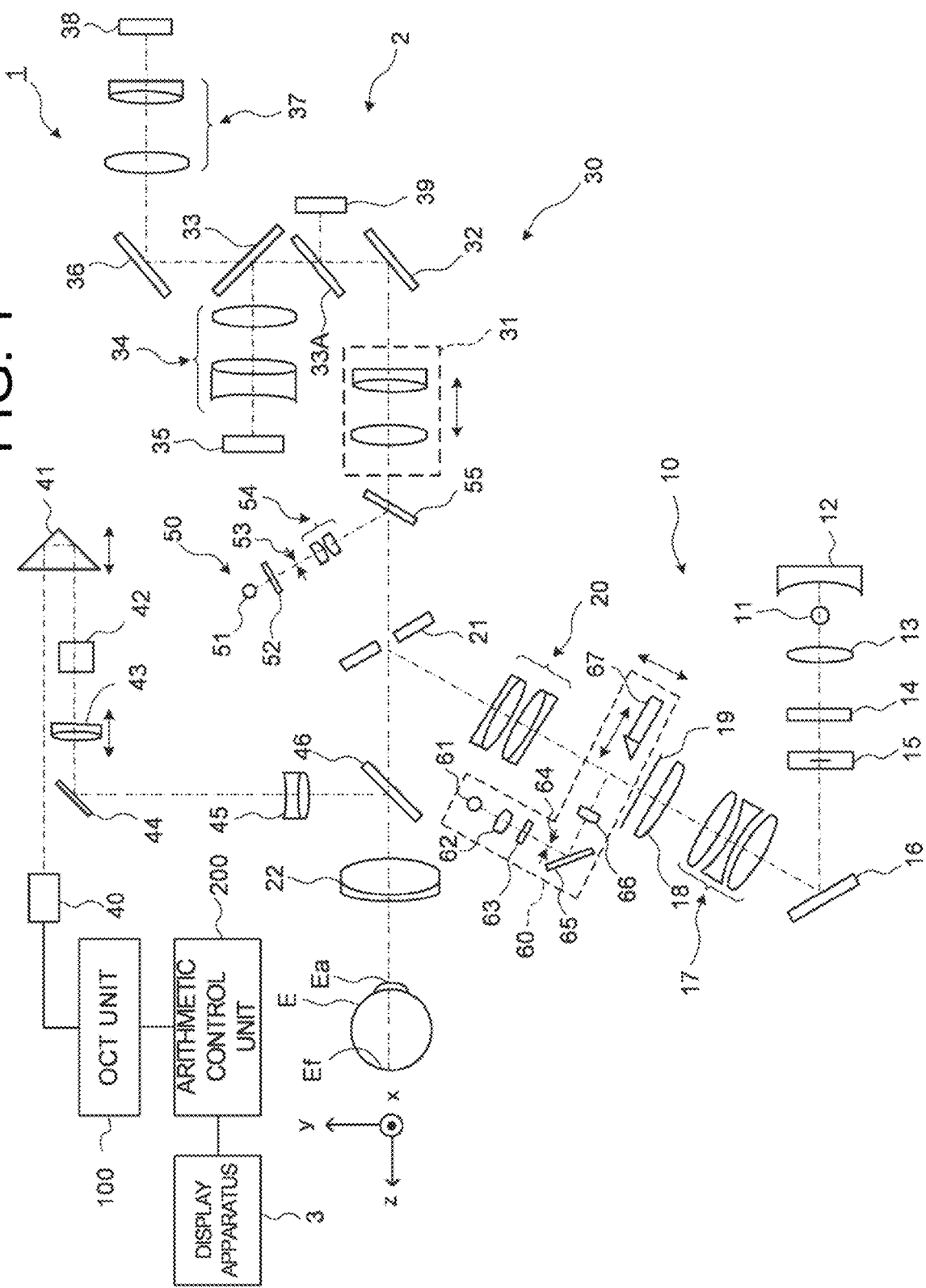
FIG. 1 is a schematic diagram illustrating an example of a configuration of an ophthalmologic apparatus according to embodiments.

In the conventional method, the contour shape of the acquired tomographic image is transformed into a rectangle. Therefore, the wider the angle of view is, the greater the difference between the shape of the predetermined site in the tomographic image and the actual shape becomes.

Further, in case of measuring an intraocular distance between two points in the acquired tomographic image, for example, the intraocular distance is obtained by multiplying the number of pixels between the two points by the pixel size, the pixel size being specific to the apparatus. Therefore, the error in the intraocular distance increases depending on the depth position.

According to some embodiments of the present invention, a new technique for specifying an actual shape or the like of a predetermined site inside an eye can be provided.

Referring now to the drawings, exemplary embodiments of an ophthalmologic information processing apparatus, an ophthalmologic apparatus, an ophthalmologic information processing method, and a program according to the present invention are described below. Any of the contents of the documents cited in the present specification and arbitrary known techniques may be applied to the embodiments below.

An ophthalmologic information processing apparatus according to embodiments corrects an OCT image of a subject's eye, two-dimensional scan data of the subject's eye, or three-dimensional scan data of the subject's eye. The OCT image, the two-dimensional scan data, or the three-dimensional scan data is acquired by scanning inside the subject's eye using an optical scanner. The optical scanner is arranged at a position optically conjugate with a predetermined site in the subject's eye. Examples of the predetermined site include a pupil. The OCT image is a two-dimensional image or a three-dimensional image. Examples of the OCT image include a tomographic image of a fundus and a three-dimensional image of the fundus. The OCT image or the scan data is acquired using optical coherence tomography (OCT). The OCT image is formed by arranging a plurality of A-scan images acquired by scanning inside the subject's eye with measurement light deflected around the predetermined site of the subject's eye. A scan center position of the scanning is arranged at the predetermined site. The two-dimensional scan data or the three-dimensional scan data is formed by arranging a plurality of A-scan data acquired by scanning inside the subject's eye with measurement light deflected around the predetermined site of the subject's eye. The scan center position of the scanning is arranged at the predetermined site.

The ophthalmologic information processing apparatus specifies a transformation position along an A-scan direction (traveling direction of the measurement light passing through the predetermined site of the subject's eye). Here, the transformation position corresponds to a pixel position in the OCT image, or a scan position in the two-dimensional scan data or the three-dimensional scan data. The ophthalmologic information processing apparatus transforms the pixel position or the scan position into the transformation position specified based on the pixel position or the like. The transformation position is a position in a predetermined coordinate system. The predetermined coordinate system is defined by two or more coordinate axes including an coordinate axis in the same axial direction as the scan direction of at least one A-scan.

In some embodiments, the ophthalmologic information processing apparatus specifies the transformation position based on a parameter representing optical characteristics of the subject's eye. In some embodiments, the ophthalmologic information processing apparatus specifies at least one of a component of a first axis direction of the transformation position and a component of a second axis direction of the transformation position, the second axis direction intersecting the first axis direction, in a predetermined coordinate system, based on a scan radius in the A-scan direction, a scan angle, a depth range that can be measured using OCT and the pixel position or the scan position.

This allows to correct the shape of the intraocular site such as the fundus represented by the OCT image or the scan data to a shape along the actual scan. In particular, the actual shape can be easily grasped from the OCT image or the scan data, which is acquired using a wide-angle imaging system or an observation system. Further, morphology information representing the morphology of the subject's eye can also be acquired as the information representing the actual morphology, using the corrected OCT image, the corrected two-dimensional scan data, or the corrected three-dimensional scan data.

An ophthalmologic information processing method according to the embodiments includes one or more steps for realizing the processing executed by a processor (computer) in the ophthalmologic information processing apparatus according to the embodiments. A program according to the embodiments causes the processor to execute each step of the ophthalmologic information processing method according to the embodiments.

The term "processor" as used herein refers to a circuit such as, for example, a central processing unit (CPU), a graphics processing unit (GPU), an application specific integrated circuit (ASIC), and a programmable logic device (PLD). Examples of PLD include a simple programmable logic device (SPLD), a complex programmable logic device (CPLD), and a field programmable gate array (FPGA). The processor realizes, for example, the function according to the embodiments by reading out a computer program stored in a storage circuit or a storage device and executing the computer program.

In this specification, an image acquired using OCT may be collectively referred to as an "OCT image". Also, the measurement operation for forming OCT images may be referred to as OCT measurement.

Hereinafter, the case where a tomographic is acquired as the OCT image of the subject's eye will be described. However, the same applies to the case where the three-dimensional image, the two-dimensional scan data, or the three-dimensional scan data is acquired using OCT.

Further, hereinafter, the case where the ophthalmologic apparatus according to the embodiments has the function of the ophthalmologic information processing apparatus according to the embodiments will be described. However, the ophthalmologic information processing apparatus according to the embodiments may be configured to acquire the OCT image, the two-dimensional scan data, or the three-dimensional scan data from an external ophthalmologic apparatus.

Hereinafter, in the embodiments, the case of using the swept source type OCT method in the measurement or the imaging (photographing) using OCT will be described. However, the configuration according to the embodiments can also be applied to an ophthalmologic apparatus using other type of OCT (for example, spectral domain type OCT or time domain OCT).

The ophthalmologic apparatus according to some embodiments includes any one or more of an ophthalmologic imaging apparatus, an ophthalmologic measuring apparatus, and an ophthalmologic therapy apparatus. The ophthalmologic imaging apparatus included in the ophthalmologic apparatus according to some embodiments includes, for example, any one or more of a fundus camera, a scanning laser ophthalmoscope, a slit lamp ophthalmoscope, a surgical microscope, and the like. Further, the ophthalmologic measuring apparatus included in the ophthalmologic apparatus according to some embodiments includes any one or more of an eye refractivity examination apparatus, a tonometer, a specular microscope, a wave-front analyzer, a perimeter, a microperimeter, and the like, for example. Further, the ophthalmologic therapy apparatus included in the ophthalmologic apparatus according to some embodiments includes any one or more of a laser therapy apparatus, a surgical apparatus, a surgical microscope, and the like, for example.

The ophthalmologic apparatus according to the following embodiments includes an OCT apparatus and a fundus camera. The OCT apparatus can perform OCT measurement. Alternatively, the configuration according to the following embodiments may be applied to a single-functional OCT apparatus.

Hereinafter, an ophthalmologic apparatus capable of performing OCT measurement on a fundus of the subject's eye will be described as an example. However, the ophthalmologic apparatus according to the embodiments may be capable of performing OCT measurement on an anterior segment of the subject's eye. In some embodiments, a measurement site of the OCT measurement and/or a range of the OCT measurement are changed by moving a lens for changing focal position of the measurement light. In some embodiments, the ophthalmologic apparatus has a configuration capable of performing OCT measurement on the fundus, OCT measurement on the anterior segment, and OCT measurement on the whole eyeball including the fundus and anterior segment, by adding one or more attachments (objective lens, front lens, etc.). In some embodiments, in the ophthalmologic apparatus for measuring fundus, OCT measurement is performed on the anterior segment, by making the measurement light incident on the subject's eye, the measurement light having been converted into a parallel light flux by arranging a front lens between the objective lens and the subject's eye.

<Configuration>
[Optical System]

As shown in FIG. 1, the ophthalmologic apparatus 1 includes a fundus camera unit 2, an OCT unit 100, and an arithmetic control unit 200. The fundus camera unit 2 is provided with an optical system and a mechanism for acquiring front images of a subject's eye E. The OCT unit 100 is provided with a part of an optical system and a mechanism for performing OCT. Another part of the optical system and the mechanism for performing OCT are provided in the fundus camera unit 2. The arithmetic control unit 200 includes one or more processors for performing various kinds of arithmetic processing and control processing. In addition to these elements, an arbitrary element or a unit, such as a member (chin rest, forehead pad, etc.) for supporting a face of the subject, a lens unit (for example, an attachment for an anterior segment OCT) for switching the target site of OCT, and the like, may be provided in the ophthalmologic apparatus 1. In some embodiments, the lens unit is configured to be manually inserted and removed between the subject's eye E and an objective lens 22 described later. In some embodiments, the lens unit is configured to be automatically inserted and removed between the subject's eye E and the objective lens 22 described later, under the control of the controller 210 described later.

In some embodiments, the ophthalmologic apparatus a includes a display apparatus 3. The display apparatus 3 displays a processing result (for example, an OCT image or the like) obtained by the arithmetic control unit 200, an image obtained by the fundus camera unit 2, operation guidance information for operating the ophthalmologic apparatus 1, and the like.

[Fundus Camera Unit]

The fundus camera unit 2 is provided with an optical system for imaging (photographing) a fundus Ef of the subject's eye E. An image (called fundus image, fundus photograph, etc.) of the fundus Ef to be obtained is a front image such as an observation image, a photographic image, or the like. The observation image is obtained by moving image shooting using near infrared light. The photographic image is a still image using flash light. Furthermore, the fundus camera unit 2 can obtain the front image (anterior segment image) by photographing (imaging) an anterior segment Ea of the subject's eye E.

The fundus camera unit 2 includes an illumination optical system 10 and an imaging (photographing) optical system 30. The illumination optical system 10 projects illumination light onto the subject's eye E. The imaging optical system 30 detects returning light of the illumination light from the subject's eye E. Measurement light from the OCT unit 100 is guided to the subject's eye E through an optical path in the fundus camera unit 2. Returning light of the measurement light is guided to the OCT unit 100 through the same optical path.

Light (observation illumination light) emitted from the observation light source 11 of the illumination optical system 10 is reflected by a reflective mirror 12 having a curved reflective surface, and becomes near-infrared light after penetrating a visible cut filter 14 via a condenser lens 13. Further, the observation illumination light is once converged near an imaging light source 15, is reflected by a mirror 16, and passes through relay lenses 17 and 18, a diaphragm 19, and a relay lens 20. Then, the observation illumination light is reflected on the peripheral part (the surrounding area of a hole part) of a perforated mirror 21, penetrates a dichroic mirror 46, and is refracted by an objective lens 22, thereby illuminating the subject's eye E (fundus Ef or anterior segment Ea). Returning light of the observation illumination light reflected from the subject's eye E is refracted by the objective lens 22, penetrates the dichroic mirror 46, passes through the hole part formed in the center region of the perforated mirror 21, penetrates a dichroic mirror 55. The returning light penetrating the dichroic mirror 55 travels through a photography focusing lens 31 and is reflected by a mirror 32. Further, this returning light penetrates a half mirror 33A, is reflected by a dichroic mirror 33, and forms an image on the light receiving surface of an image sensor 35 by a condenser lens 34. The image sensor 35 detects the returning light at a predetermined frame rate. It should be noted that the focus of the imaging optical system 30 is adjusted so as to coincide with the fundus Ef or the anterior segment Ea.

Light (imaging illumination light) emitted from the imaging light source 15 is projected onto the fundus Ef via the same route as that of the observation illumination light. Returning light of the imaging illumination light from the subject's eye E is guided to the dichroic mirror 33 via the same route as that of the observation illumination light, penetrates the dichroic mirror 33, is reflected by a mirror 36, and forms an image on the light receiving surface of the image sensor 38 by a condenser lens 37.

A liquid crystal display (LCD) 39 displays a fixation target and a visual target used for visual acuity measurement. Part of light output from the LCD 39 is reflected by the half mirror 33A, is reflected by the mirror 32, travels through the photography focusing lens 31 and the dichroic mirror 55, and passes through the hole part of the perforated mirror 21. The light flux (beam) having passed through the hole part of the perforated mirror 21 penetrates the dichroic mirror 46, and is refracted by the objective lens 22, thereby being projected onto the fundus Ef.

By changing the display position of the fixation target on the screen of the LCD 39, the fixation position of the subject's eye E can be changed. Examples of the fixation position include a fixation position for acquiring an image centered at a macula, a fixation position for acquiring an image centered at an optic disc, a fixation position for acquiring an image centered at a fundus center between the macula and the optic disc, a fixation position for acquiring an image of a site (fundus peripheral part) far away from the macula, and the like. The ophthalmologic apparatus 1 according to some embodiments includes GUI (Graphical User Interface) and the like for designating at least one of such fixation positions. The ophthalmologic apparatus 1 according to some embodiments includes GUI etc. for manually moving the fixation position (display position of the fixation target).

The configuration for presenting the movable fixation target to the subject's eye E is not limited to the display device such LCD or the like. For example, the movable fixation target can be generated by selectively turning on a plurality of light sources of a light source array (light emitting diode (LED) array or the like). Alternatively, the movable fixation target can be generated using one or more movable light sources.

Further, the ophthalmologic apparatus 1 may be provided with one or more external fixation light sources. One of the one or more external fixation light sources can project fixation light onto a fellow eye of the subject's eye E. A projected position of the fixation light on the fellow eye can be changed. By changing the projected position of the fixation light on the fellow eye, the fixation position of the subject's eye E can be changed. The fixation position projected by the external fixation light source(s) may be the same as the fixation position of the subject's eye E using the LCD 39. For example, the movable fixation target can be generated by selectively turning on a plurality of external fixation light sources. Alternatively, the movable fixation target can be generated using one or more movable external fixation light sources.

The alignment optical system 50 generates an alignment indicator for alignment of the optical system with respect to the subject's eye E. Alignment light emitted from an LED 51 travels through the diaphragms 52 and 53 and the relay lens 54, is reflected by the dichroic mirror 55, and passes through the hole part of the perforated mirror 21. The alignment light having passed through the hole part of the perforated mirror 21 penetrates the dichroic mirror 46, and is projected onto the subject's eye E by the objective lens 22. Corneal reflection light of the alignment light is guided to the image sensor 35 through the same route as the returning light of the observation illumination light. Manual alignment or automatic alignment can be performed based on the received light image (alignment indicator image) thereof.

The focus optical system 60 generates a split indicator for adjusting the focus with respect to the subject's eye E. The focus optical system 60 is movable along an optical path (illumination optical path) of the illumination optical system 10 in conjunction with the movement of the photography focusing lens 31 along an optical path (imaging optical path) of the imaging optical system 30. The reflection rod 67 can be inserted and removed into and from the illumination optical path. To conduct focus adjustment, the reflective surface of the reflection rod 67 is arranged in a slanted position on the illumination optical path. Focus light emitted from an LED 61 passes through a relay lens 62, is split into two light beams by a split indicator plate 63, passes through a two-hole diaphragm 64, is reflected by a mirror 65, and is reflected after an image is once formed on the reflective surface of the reflection rod 67 by a condenser lens 66. Further, the focus light travels through the relay lens 20, is reflected by the perforated mirror 21, penetrates the dichroic mirror 46, and is refracted by the objective lens 22, thereby being projected onto the fundus Ef. Fundus reflection light of the focus light is guided to the image sensor 35 through the same route as the corneal reflection light of the alignment light. Manual focus or automatic focus can be performed based on the received light image (split indicator image) thereof The dichroic mirror 46 combines an optical path for fundus photography and an optical path for OCT. The dichroic mirror 46 reflects light of wavelength band used in OCT, and transmits light for fundus photography. The optical path for OCT (optical path of measurement light) is provided with, in order from the OCT unit 100 side to the dichroic mirror 46 side, a collimator lens unit 40, an optical path length changing unit 41, an optical scanner 42, an OCT focusing lens 43, a mirror 44, and a relay lens 45.

The optical path length changing unit 41 is movable in directions indicated by the arrow in FIG. 1, thereby changing the length of the optical path for OCT. This change in the optical path length is used for correcting the optical path length according to the axial length, adjusting the interference state, or the like. The optical path length changing unit 41 includes a corner cube and a mechanism for moving the corner cube.

The optical scanner 42 is disposed at a position optically conjugate with the pupil of the subject's eye E. The optical scanner 42 deflects the measurement light traveling along the OCT optical path. That is, the optical scanner 42 deflects the measurement light for scanning inside the subject's eye E while changing the scan angle within a predetermined deflection angle range with the pupil (or the vicinity thereof) of the subject's eye E as the scan center position. The optical scanner 42 can deflect the measurement light in a one-dimensionally or two-dimensional manner.

In case that the optical scanner 42 deflects the measurement light in a one-dimensionally manner, the optical scanner 42 includes a galvano scanner capable of deflecting the measurement light in a predetermined deflection direction within a predetermined deflection angle range. In case that the optical scanner deflects the measurement light LS in a two-dimensionally manner, the optical scanner 42 includes a first galvano scanner and a second galvano scanner. The first galvano scanner deflects the measurement light so as to scan a photographing (imaging) site (fundus Ef or the anterior segment) in a horizontal direction orthogonal to the optical axis of the OCT optical system 8. The second galvano scanner deflects the measurement light deflected by the first galvano mirror so as to scan the photographing site in a vertical direction orthogonal to the optical axis of the OCT optical system 8. Examples of scan mode with the measurement light performed by the optical scanner 42 include horizontal scan, vertical scan, cross scan, radial scan, circle scan, concentric scan, helical (spiral) scan, and the like.

The OCT focusing lens 43 is moved along the optical path of the measurement light in order to perform focus adjustment of the optical system for OCT. The OCT focusing lens 43 can move within a moving range. The moving range includes a first lens position for placing the focal position of the measurement light at the fundus Ef or near the fundus Ef of the subject's eye E and a second lens position for making the measurement light projected onto the subject's eye E a parallel light beam. The movement of the photography focusing lens 31, the movement of the focus optical system 60, and the movement of the OCT focusing lens 43 can be controlled in conjunction with each other.

[Oct Unit]

Figure 2:
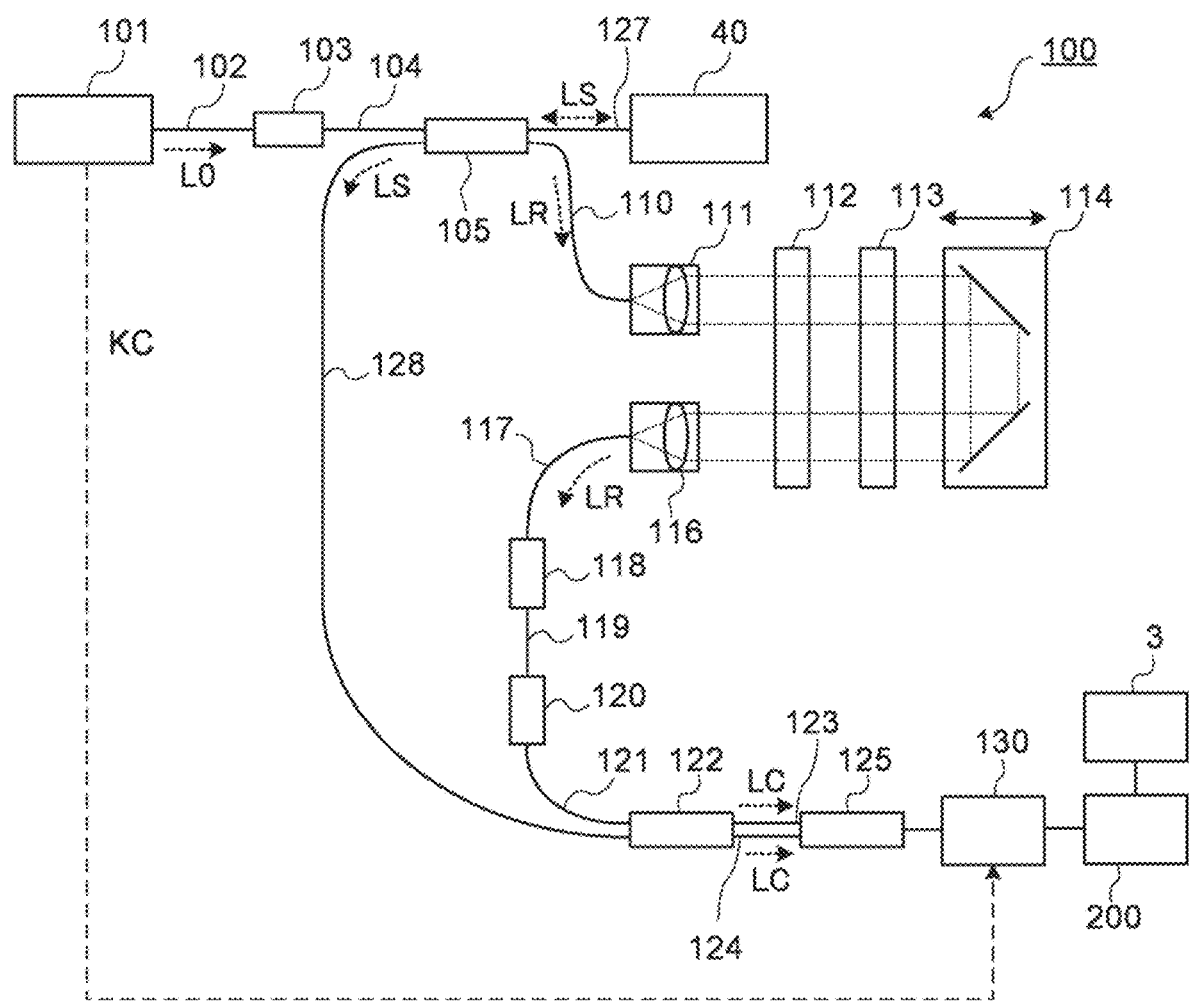
FIG. 2 is a schematic diagram illustrating an example of a configuration of the ophthalmologic apparatus according to the embodiments.

An example of the configuration of the OCT unit 100 is shown in FIG. 2. The OCT unit 100 is provided with an optical system for acquiring OCT images of the subject's eye E. The optical system includes an interference optical system that splits light from a wavelength sweeping type (i.e., a wavelength scanning type) light source into measurement light and reference light, makes the measurement light returning from the subject's eye E and the reference light having traveled through the reference optical path interfere with each other to generate interference light, and detects the interference light. The detection result of the interference light obtained by the interference optical system (i.e., the detection signal) is an interference signal indicating the spectrum of the interference light, and is sent to the arithmetic control unit 200.

Like swept source type ophthalmologic apparatuses commonly used, the light source unit 101 includes a wavelength sweeping type (i.e., a wavelength scanning type) light source capable of sweeping (scanning) the wavelengths of emitted light. The wavelength sweeping type light source includes a laser light source that includes a resonator. The light source unit 101 temporally changes the output wavelengths within the near-infrared wavelength bands that cannot be visually recognized with human eyes.

Light L0 output from the light source unit 101 is guided to the polarization controller 103 through the optical fiber 102, and the polarization state of the light L0 is adjusted. The polarization controller 103, for example, applies external stress to the looped optical fiber 102 to thereby adjust the polarization state of the light L0 guided through the optical fiber 102.

The light L0 whose the polarization state has been adjusted by the polarization controller 103 is guided to the fiber coupler 105 through the optical fiber 104, and is split into the measurement light LS and the reference light LR.

The reference light LR is guided to the collimator 111 through the optical fiber 110. The reference light LR is converted into a parallel light beam by the collimator 111. Then, the reference light LR is guided to the optical path length changing unit 114 via an optical path length correction member 112 and a dispersion compensation member 113. The optical path length correction member 112 acts so as to match the optical path length of the reference light LR with the optical path length of the measurement light LS. The dispersion compensation member 113 acts so as to match the dispersion characteristics between the reference light LR and the measurement light LS.

The optical path length changing unit 114 is movable in directions indicated by the arrow in FIG. 2, thereby changing the length of the optical path of the reference light LR. Through such movement, the length of the optical path of the reference light LR is changed. The change in the optical path length is used for the correction of the optical path length according to the axial length of the subject's eye E, for the adjustment of the interference state, or the like. The optical path length changing unit 114 includes, for example, a corner cube and a movement mechanism for moving the corner cube. In this case, the corner cube in the optical path length changing unit 114 changes the traveling direction of the reference light LR that has been made into the parallel light flux by the collimator 111 in the opposite direction. The optical path of the reference light LR incident on the corner cube and the optical path of the reference light LR emitted from the corner cube are parallel.

The reference light LR that has traveled through the optical path length changing unit 114 passes through the dispersion compensation member 113 and the optical path length correction member 112, is converted from the parallel light beam to the convergent light beam by a collimator 116, and enters an optical fiber 117. The reference light LR that has entered the optical fiber 117 is guided to the polarization controller 118. With the polarization controller 118, the polarization state of the reference light LR is adjusted. The polarization controller 118 has the same configuration as, for example, the polarization controller 103. The reference light LR whose the polarization state has been adjusted by the polarization controller 118 is guided to the attenuator 120 through the optical fiber 119, and the light amount thereof is adjusted by the attenuator 120 under the control of the arithmetic control unit 200. The reference light LR whose light amount has been adjusted by the attenuator 120 is guided to the fiber coupler 122 by the optical fiber 121.

The configuration shown in FIG. 1 and FIG. 2 includes both the optical path length changing unit 41 that changes the length of the optical path of the measurement light LS (i.e., measurement optical path or measurement arm) and the optical path length changing unit 114 that changes the length of the optical path of the reference light LR (i.e., reference optical path or reference arm). However, any one of the optical path length changing units 41 and 114 may be provided. The difference between the measurement optical path length and the reference optical path length can be changed by using other optical members.

Meanwhile, the measurement light LS generated by the fiber coupler 105 is guided through the optical fiber 127, and is made into the parallel light beam by the collimator lens unit 40. The measurement light LS made into the parallel light flux is guided to the dichroic mirror 46 via the optical path length changing unit 41, the optical scanner 42, the OCT focusing lens 43, the mirror 44, and the relay lens 45. The measurement light LS guided to the dichroic mirror 46 is reflected by the dichroic mirror 46, refracted by the objective lens 22, and projected onto the subject's eye E. The measurement light LS is scattered (and reflected) at various depth positions of the subject's eye E. The returning light of the measurement light LS including such backscattered light advances through the same path as the outward path in the opposite direction and is led to the fiber coupler 105, and then reaches the fiber coupler 122 through the optical fiber 128.

The fiber coupler 122 combines (interferes) the measurement light LS incident through the optical fiber 128 and the reference light LR incident through the optical fiber 121 to generate interference light. The fiber coupler 122 generates a pair of interference light LC by splitting the interference light generated from the measurement light LS and the reference light LR at a predetermined splitting ratio (for example, 1:1). The pair of the interference light LC emitted from the fiber coupler 122 is guided to the detector 125 through the optical fibers 123 and 124, respectively.

The detector 125 is, for example, a balanced photodiode that includes a pair of photodetectors for respectively detecting the pair of interference light LC and outputs the difference between the pair of detection results obtained by the pair of photodetectors. The detector 125 sends the detection result (i.e., interference signal) to the data acquisition system (DAQ) 130. A clock KC is supplied from the light source unit 101 to the DAQ 130. The clock KC is generated in the light source unit 101 in synchronization with the output timing of each wavelength sweeping (scanning) within a predetermined wavelength range performed by the wavelength sweeping type light source. For example, the light source unit 101 optically delays one of the two pieces of branched light obtained by branching the light L0 of each output wavelength, and then generates the clock KC based on the result of the detection of the combined light of the two pieces of branched light. The DAQ 130 performs sampling of the detection result obtained by the detector 125 based on the clock KC. The DAQ 130 sends the result of the sampling of the detection result obtained by the detector 125 to the arithmetic control unit 200. For example, the arithmetic control unit 200 performs the Fourier transform etc. on the spectral distribution based on the detection result obtained by the detector 125 for each series of wavelength scanning (i.e., for each A-line). With this, the reflection intensity profile for each A-line is formed. In addition, the arithmetic control unit 200 forms image data by applying imaging processing to the reflection intensity profiles for the respective A-lines.

[Arithmetic Control Unit]

The arithmetic control unit 200 analyzes the detection signals fed from the DAQ 130 to form an OCT image or scan data of the fundus Ef (or the anterior segment Ea). The arithmetic processing therefor is performed in the same manner as in the conventional swept-source-type OCT apparatus.

Further, the arithmetic control unit 200 controls each part of the fundus camera unit 2, the display apparatus 3, and the OCT unit 100.

Also, as the control of the fundus camera unit 2, the arithmetic control unit 200 performs following controls: the operation control of the observation light source 11, of the imaging light source 15 and of the LEDs 51 and 61; the operation control of the LCD 39; the movement control of the photography focusing lens 31; the movement control of the OCT focusing lens 43; the movement control of the reflection rod 67; the movement control of the focus optical system 60; the movement control of the optical path length changing unit 41; the operation control of the optical scanner 42, and the like.

For example, the arithmetic control unit 200 controls the display apparatus 3 to display the OCT image of the subject's eye E.

Further, as the control of the OCT unit 100, the arithmetic control unit 200 controls: the operation of the light source unit 101; the operation of the optical path length changing unit 114; the operations of the attenuator 120; the operation of the polarization controllers 103 and 118; the operation of the detector 125; the operation of the DAQ 130; and the like.

As in the conventional computer, the arithmetic control unit 200 includes a processor, RAM, ROM, hard disk drive, and communication interface, for example. A storage device such as the hard disk drive stores a computer program for controlling the ophthalmologic apparatus 1. The arithmetic control unit 200 may include various kinds of circuitry such as a circuit board for forming OCT images. In addition, the arithmetic control unit 200 may include an operation device (or an input device) such as a keyboard and a mouse, and a display device such as an LCD.

The fundus camera unit 2, the display apparatus 3, the OCT unit 100, and the arithmetic control unit 200 may be integrally provided (i.e., in a single housing), or they may be separately provided in two or more housings.

[Control System]

Figure 3:
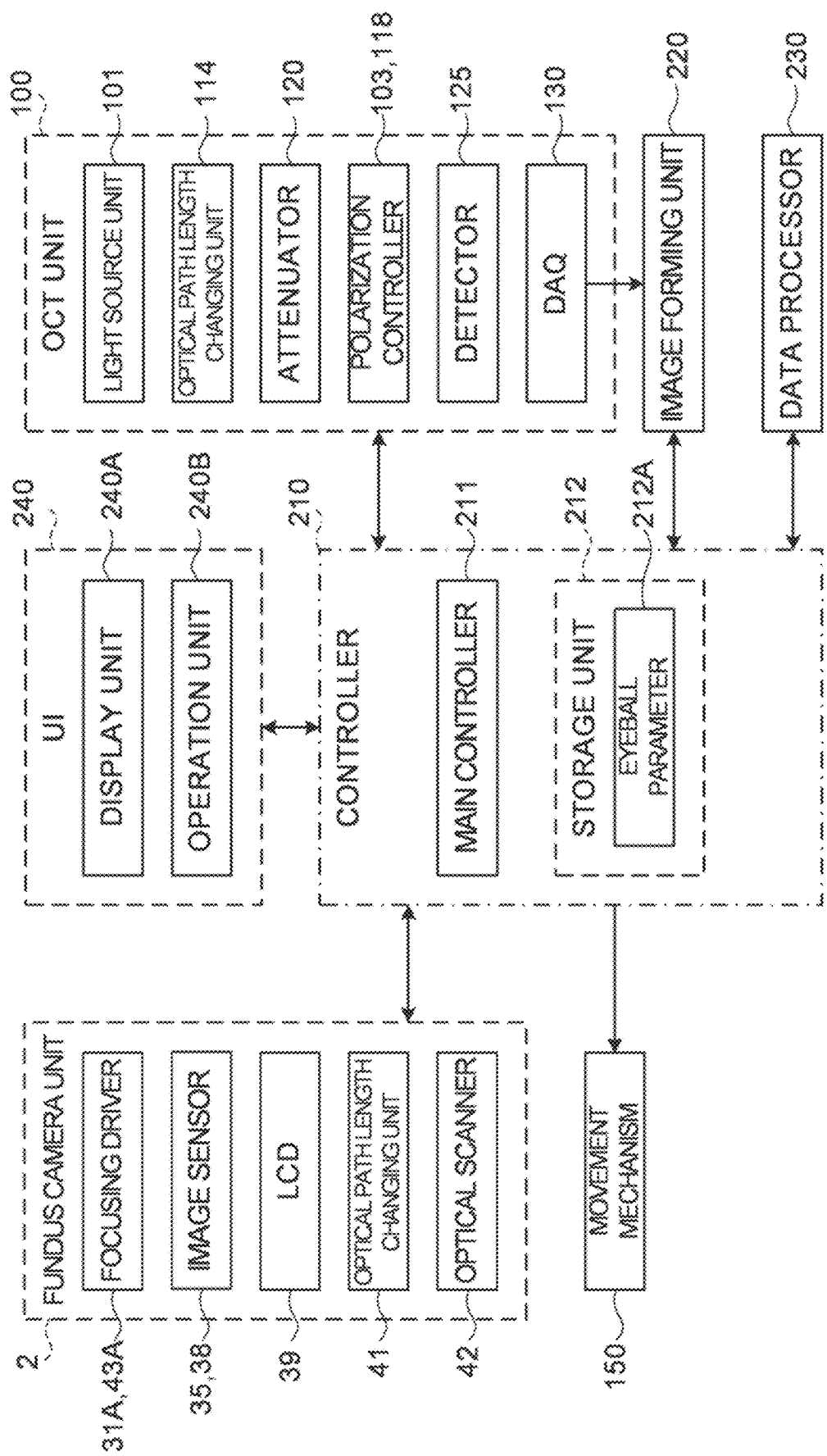
FIG. 3 is a schematic block diagram illustrating an example of the configuration of the ophthalmologic apparatus according to the embodiments.
Figure 4:
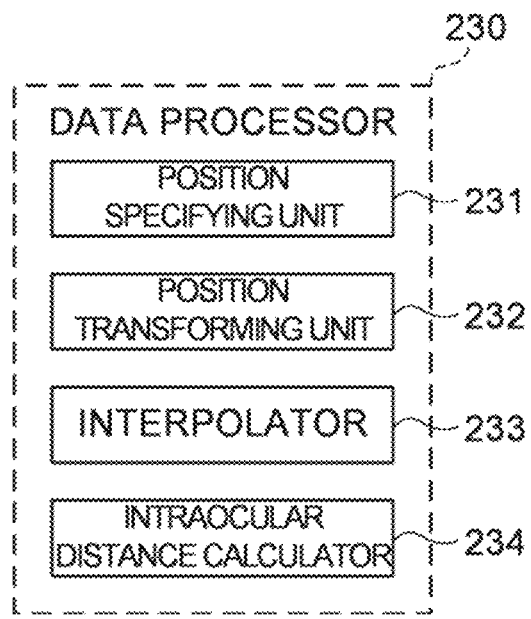
FIG. 4 is a schematic block diagram illustrating an example of the configuration of the ophthalmologic apparatus according to the embodiments.

FIGS. 3 and 4 illustrate a configuration example of a control system of the ophthalmologic apparatus 1. In FIGS. 3 and 4, a part of the components included in the ophthalmologic apparatus 1 is omitted.

(Controller)

The controller 210 executes various controls. The controller 210 includes a main controller 211 and a storage unit 212.

(Main Controller)

The main controller 211 includes a processor and controls each part of the ophthalmologic apparatus 1. For example, the main controller 211 controls components of the fundus camera unit 2 such as focusing drivers 31A and 43A, the image sensors 35 and 38, the LCD 39, the optical path length changing unit 41, the optical scanner 42, and a movement mechanism 150 for moving the optical system. Further, the main controller 211 controls components of the OCT unit 100 such as the light source unit 101, the optical path length changing unit 114, the attenuator 120, the polarization controllers 103 and 118, the detector 125, and the DAQ 130.

For example, the main controller 211 controls the LCD 39 to display the fixation target at a position on the screen of the LCD 39 corresponding the fixation position set manually or automatically. Moreover, the main controller 211 can change the display position of the fixation target displayed on the LCD 39 (in a continuous manner or in a phased manner). Thereby, the fixation target can be moved (that is, the fixation position can be changed). The display position of the fixation target and movement mode of the fixation target are set manually or automatically. Manual setting is performed using GUI, for example. Automatic setting is performed by the data processor 230, for example.

The focusing driver 31A moves the photography focusing lens 31 in the direction along the optical axis of the imaging optical system 30, and moves the focus optical system 60 in the direction along the optical axis of the illumination optical system 10. With this, the focus position of the imaging optical system 30 is changed. The focusing driver 31A may include a dedicated mechanism for moving the photography focusing lens 31 and a dedicated mechanism for moving the focus optical system 60. The focusing driver 31A is controlled when performing focus adjustment or the like.

The focusing driver 43A moves the OCT focusing lens 43 in the optical axis direction of the measurement optical path. As a result, the focus position of the measurement light LS is changed. For example, the focus position of the measurement light LS can be arranged at the fundus Ef or near the fundus Ef by moving the OCT focusing lens 43 to the first lens position. For example, the focus position of the measurement light LS can be arranged at a far point position by moving the OCT focusing lens 43 to the second lens position. The focus position of the measurement light LS corresponds to the depth position (z position) of the beam waist of the measurement light LS.

The movement mechanism 150 three-dimensionally moves at least the fundus camera unit 2 (optical system), for example. In a typical example, the movement mechanism 150 includes a mechanism for moving at least the fundus camera unit 2 in the x direction (left-right direction, horizontal direction), a mechanism for moving it in the y direction (up-down direction, vertical direction), and a mechanism for moving it in the z direction (depth direction, front-back direction). The mechanism for moving in the x direction includes a x stage movable in the x direction and a x movement mechanism for moving the x stage, for example. The mechanism for moving in the y direction includes a y stage movable in the y direction and a y movement mechanism for moving the y stage, for example. The mechanism for moving in the z direction includes a z stage movable in the z direction and a z movement mechanism for moving the z stage, for example. Each movement mechanism includes an actuator such as a pulse motor, and operates under the control of the main controller 211.

The control for the movement mechanism 150 is used for alignment and tracking. Here, tracking is to move the optical system of the apparatus according to the movement of the subject's eye E. To perform tracking, alignment and focus adjustment are performed in advance. The tracking is a function of maintaining a suitable positional relationship in which alignment and focusing are matched by causing the position of the optical system of the apparatus and the like to follow the eye movement. In some embodiments, the movement mechanism 150 is configured to be controlled to change the optical path length of the reference light (that is, the difference of the optical path length between the optical path of the measurement light and the optical path of the reference light).

In the case of manual alignment, a user operates a user interface (UI) 240 described later to relatively move the optical system and subject's eye E so as to cancel the displacement of the subject's eye E with respect to the optical system. For example, the main controller 211 controls the movement mechanism 150 to relatively move the optical system and the subject's eye E by outputting a control signal corresponding to the operation content with respect to the user interface 240 to the movement mechanism 150.

In the case of automatic alignment, the main controller 211 controls the movement mechanism 150 to relatively move the optical system and the subject's eye E so as to cancel the displacement of the subject's eye E with respect to the optical system. For example, the movement mechanism 150 is controlled so as to cancel a displacement between (a reference position of) the image of the subject's eye E acquired using imaging optical system 30 and a reference position of the optical system. In some embodiments, the main controller 211 controls the movement mechanism 150 to relatively move the optical system and the subject's eye E by outputting a control signal to the movement mechanism 150 so that the optical axis of the optical system substantially coincides with the axis of the subject's eye E and the distance of the optical system with respect to the subject's eye E is a predetermined working distance. Here, the working distance is a preset value which is called a working distance of the objective lens 22, and it means the distance between the subject's eye E and the optical system when measuring (imaging) using the optical system.

The main controller 211 controls the fundus camera unit 2 etc. to control the fundus imaging (photography) and the anterior segment imaging. Further, the main controller 211 controls the fundus camera unit 2 and the OCT unit 100 etc. to control the OCT measurement. The main controller 211 is capable of performing a plurality of preliminary operations prior to OCT measurement. Examples of the preliminary operation include alignment, rough focus adjustment, polarization adjustment, and fine focus adjustment. The plurality of preliminary operations is performed in a predetermined order. In some embodiments, the plurality of preliminary operations is performed in an order described above.

It should be noted that the types and the orders of the preliminary operations are not so limited, and they may be optional. For example, the preliminary operations may further include small-pupil judgment. The small-pupil judgment is a preliminary operation to judge whether the pupil of the subject's eye E is small or not (whether the subject's eye E is microcoria or not). The small-pupil judgment may be performed between the rough focus adjustment and the optical path length difference adjustment. In some embodiments, the small-pupil judgment includes, for example, a series of processes as follows: acquiring a front image (anterior segment image) of the subject's eye E; specifying an image region corresponding to the pupil; calculating the size (e.g., diameter, circumference length) of the pupil region; judging whether the pupil of the subject's eye E is small or not based on the calculated size (threshold processing); and controlling the diaphragm 19 when judged that the pupil of the subject's eye E is small. In some embodiments, the calculation of the size of the pupil region includes processing of circularly or elliptically approximating the pupil region.

The rough focus adjustment is a kind of focus adjustment using the split indicator. The rough focus adjustment may be performed by determining the position of the photography focusing lens 31 based on information, which is obtained by associating the eye refractive power acquired in advance with the position of the photography focusing lens 31, and a measured value of the refractive power of the subject's eye E.

The fine focus adjustment is performed on the basis of interference sensitivity of OCT measurement. For example, the fine focus adjustment can be performed by: monitoring interference intensity (interference sensitivity) of interference signal acquired by performing OCT measurement of the subject's eye E; searching the position of the OCT focusing lens 43 so as to maximize the interference intensity; and moving the OCT focusing lens 43 to the searched position.

To perform the optical path length difference adjustment, the optical system is controlled so that a predetermined position on the subject's eye E is a reference position of a measurement range in the depth direction. The control is performed on at least one of the optical path length changing units 41 and 114. Thereby, the difference of the optical path length between the measurement optical path and the reference optical path is adjusted. By setting the reference position in the optical path length difference adjustment, OCT measurement can be performed with high accuracy over a desired measurement range in the depth direction simply by changing the wavelength sweep speed.

To perform the polarization adjustment, the polarization state of the reference light LR is adjusted for optimizing the interference efficiency between the measurement light LS and the reference light LR.

(Storage Unit)

The storage unit 212 stores various types of data. Examples of the data stored in the storage unit 212 include image data of an OCT image, image data of a fundus image, scan data, image data of an anterior segment image, and subject's eye information. The subject's eye information includes information on the subject such as patient ID and name, and information on the subject's eye such as identification information of the left eye/right eye.

Further, the storage unit 212 stores an eyeball parameter 212A. The eyeball parameter 212A includes a parameter (standard value) defined by a known eyeball model such as a Gullstrand schematic eye. In some embodiments, the eyeball parameter 212A includes a parameter in which at least one of the parameters defined by a known eyeball model is replaced with the measured value of the subject's eye E. In this case, it means that the eyeball parameter 212A includes a parameter representing optical characteristics of the subject's eye E. Examples of the measured value include an axial length, a corneal thickness, a curvature radius of an anterior surface of cornea, a curvature radius of a posterior surface of cornea, an anterior chamber depth, a curvature radius of an anterior surface of a lens, a lens thickness, a curvature radius of a posterior surface of lens, a vitreous cavity length, a retinal thickness, and a choroid thickness. In some embodiments, the measured value is acquired by analyzing OCT data obtained by performing OCT measurement. The eyeball parameter 212A may include a parameter designated using the operation unit 240B described later.

In addition, the storage unit 212 stores various kinds of computer programs and data for operating the ophthalmologic apparatus 1.

(Image Forming Unit)

The image forming unit 220 performs signal processing such as the Fourier transform on sampling data obtained by sampling the detection signal from the detector 125 in the DAQ 130. With this, the reflection intensity profile for each A-line is formed. The above signal processing includes noise removal (noise reduction), filtering, fast Fourier transform (FFT), and the like. The reflection intensity profile for the A-line is an example of the A-scan data. The image forming unit 220 can form the reflection intensity profile for each A-line, and form B-scan data (two-dimensional scan data) by arranging a formed plurality of reflection intensity profiles in the B-scan direction (intersecting direction of the A-scan direction).

In some embodiments, the image forming unit 220 (or the data processor 230 described later) forms three-dimensional scan data by arranging the plurality of reflection intensity profiles formed for each A-line in the B-scan direction (for example, x direction) and a direction intersecting both of the A-scan direction and the B-scan direction (for example, y direction).

Further, the image forming unit 220 can form A-scan image (OCT image, image data) of the subject's eye E, by applying imaging processing to the reflection intensity profile in the A-line. The image forming unit 220 can form a B-scan image by arranging the plurality of A-scan images formed for each A-line in the B-scan direction (intersecting direction of the A-scan direction).

In some embodiments, the image forming unit 220 extracts data at a predetermined depth position (scan position) in each A-scan data, and forms C-scan data by arranging the extracted plurality of data in the B-scan direction (intersecting direction of the A-scan direction). In some embodiments, the image forming unit 220 extracts a pixel at a predetermined depth position (scan position) in each A-scan image, and forms a C-scan image by arranging the extracted plurality of pixels in the B-scan direction (intersecting direction of the A-scan direction).

In some embodiments, the function of the image forming unit 220 is realized by a processor. Note that "image data" and an "image" based on the image data may not be distinguished from each other in the present specification.

(Data Processor)

The data processor 230 processes data acquired through photography of the subject's eye E or data acquired through OCT measurement.

For example, the data processor 230 performs various kinds of image processing and various kinds of analysis processing on the image formed by the image forming unit 220. For example, the data processor 230 performs various types of image correction such as brightness correction. The data processor 230 performs various kinds of image processing and various kinds of analysis on images captured by the fundus camera unit 2 (e.g., fundus images, anterior segment images, etc.).

The data processor 230 performs known image processing such as interpolation for interpolating pixels in tomographic images to form three-dimensional image data of the fundus Ef. Note that image data of a three-dimensional image means image data in which the position of a pixel is defined by a three-dimensional coordinate system. Examples of the image data of the three-dimensional image include image data defined by voxels three-dimensionally arranged. Such image data is referred to as volume data or voxel data. When displaying an image based on volume data, the data processor 230 performs rendering (volume rendering, maximum intensity projection (MIP), etc.) on the volume data, thereby forming image data of a pseudo three-dimensional image viewed from a particular line of sight. The pseudo three-dimensional image is displayed on the display device such as a display unit 240A.

The three-dimensional image data may be stack data of a plurality of tomographic images. The stack data is image data formed by three-dimensionally arranging tomographic images along a plurality of scan lines based on positional relationship of the scan lines. That is, the stack data is image data formed by representing tomographic images, which are originally defined in their respective two-dimensional coordinate systems, by a single three-dimensional coordinate system. That is, the stack data is image data formed by embedding tomographic images into a single three-dimensional space.

The data processor 230 can form a B-mode image (longitudinal cross-sectional image, axial cross-sectional image) in an arbitrary cross section, a C-mode image (transverse section image, horizontal cross-sectional image) in an arbitrary cross section, a projection image, a shadowgram, etc., by performing various renderings on the acquired three-dimensional data set (volume data, stack data, etc.). An image in an arbitrary cross section such as the B-mode image or the C-mode image is formed by selecting pixels (voxels) on a designated cross section from the three-dimensional data set. The projection image is formed by projecting the three-dimensional data set in a predetermined direction (z direction, depth direction, axial direction). The shadowgram is formed by projecting a part of the three-dimensional data set (for example, partial data corresponding to a specific layer) in a predetermined direction. An image having a viewpoint on the front side of the subject's eye, such as the C-mode image, the projection image, and the shadowgram, is called a front image (en-face image).

The data processor 230 can build (form) the B-mode image or the front image (blood vessel emphasized image, angiogram) in which retinal blood vessels and choroidal blood vessels are emphasized (highlighted), based on data (for example, B-scan image data) acquired in time series by OCT. For example, the OCT data in time series can be acquired by repeatedly scanning substantially the same site of the subject's eye E.

In some embodiments, the data processor 230 compares the B-scan images in time series acquired by B-scan for substantially the same site, converts the pixel value of a change portion of the signal intensity into a pixel value corresponding to the change portion, and builds the emphasized image in which the change portion is emphasized. Further, the data processor 230 forms an OCTA image by extracting information of a predetermined thickness at a desired site from a plurality of built emphasized images and building as an en-face image.

An image (for example, a three-dimensional image, a B-mode image, a C-mode image, a projection image, a shadowgram, and an OCTA image) generated by the data processor 230 is also included in the OCT image.

Further, the data processor 230 determines the focus state of the measurement light LS in fine focus adjustment control by analyzing the detection result of the interference light obtained by the OCT measurement. For example, the main controller 211 performs repetitive OCT measurements while controlling the focusing driver 43A according to a predetermined algorithm. The data processor 230 analyzes detection results of interference light LC repeatedly acquired by the OCT measurements to calculate predetermined evaluation values relating to image quality of OCT images. The data processor 230 determines whether the calculated evaluation value is equal to or less than a threshold. In some embodiments, the fine focus adjustment is continued until the calculated evaluation value becomes equal to or less than the threshold. That is, when the evaluation value is equal to or less than the threshold, it is determined that the focus state of the measurement light LS is appropriate. And the fine focus adjustment is continued until it is determined that the focus state of the measurement light LS is appropriate.

In some embodiments, the main controller 211 monitors the intensity of the interference signal (interference intensity, interference sensitivity) acquired sequentially while acquiring the interference signal by performing the repetitive OCT measurements described above. In addition, while performing this monitoring process, the OCT focusing lens 43 is moved to find the position of the OCT focusing lens 43 in which the interference intensity is maximized. With the fine focus adjustment thus performed, the OCT focusing lens 43 can be guided to the position where the interference intensity is optimized.

Further, the data processor 230 determines the polarization state of at least one of the measurement light LS and the reference light LR by analyzing the detection result of the interference light obtained by the OCT measurement. For example, the main controller 211 performs repetitive OCT measurements while controlling at least one of the polarization controllers 103 and 118 according to a predetermined algorithm. In some embodiments, the main controller 211 controls the attenuator 120 to change an attenuation of the reference light LR. The data processor 230 analyzes detection results of interference light LC repeatedly acquired by the OCT measurements to calculate predetermined evaluation values relating to image quality of OCT images. The data processor 230 determines whether the calculated evaluation value is equal to or less than a threshold. The threshold is set in advance. Polarization adjustment is continued until the evaluation value calculated becomes equal to or less than the threshold. That is, when the evaluation value is equal to or less than the threshold, it is determined that the polarization state of the measurement light LS is appropriate. And the polarization adjustment is continued until it is determined that the polarization state of the measurement light LS is appropriate.

In some embodiments, the main controller 211 can monitor the interference intensity also in the polarization adjustment.

Further, the data processor 230 performs predetermined analysis processing on the detection result of the interference light acquired by the OCT measurement or the OCT image formed based on the detection result. Examples of the predetermined analysis processing include specifying (identification) of a predetermined site (tissue, lesion) of the subject's eye E; calculation of a distance, area, angle, ratio, or density between designated sites (distance between layers, interlayer distance); calculation by a designated formula; specifying of the shape of a predetermined site; calculation of these statistics; calculation of distribution of the measured value or the statistics; image processing based on these analysis processing results, and the like. Examples of the predetermined tissue include a blood vessel, an optic disc, a fovea, a macula, and the like. Examples of the predetermined lesion include a leukoma, a hemorrhage, and the like.

The data processor 230 performs coordinate transformation on the pixel positions in the OCT image or the scan positions in the scan data so that the site in the eye in the acquired OCT image (or the scan data) is drawn in actual shape. Further, the data processor 230 can obtain a distance between predetermined sites in the eye using the OCT image after coordinate transformation or the scan data after coordinate transformation.

Figure 5:
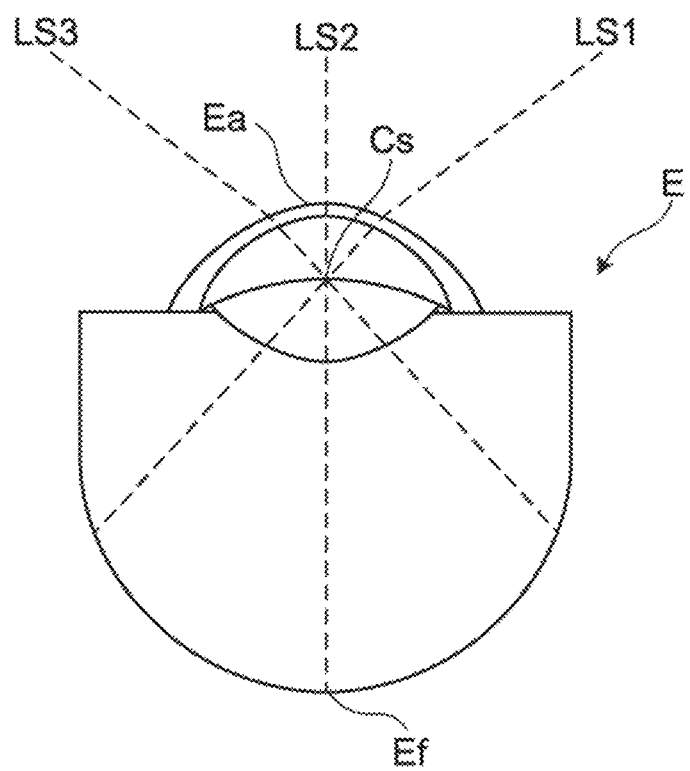
FIG. 5 is a schematic diagram for explaining processing performed by the ophthalmologic apparatus according to a comparative example of the embodiments.
Figure 6:
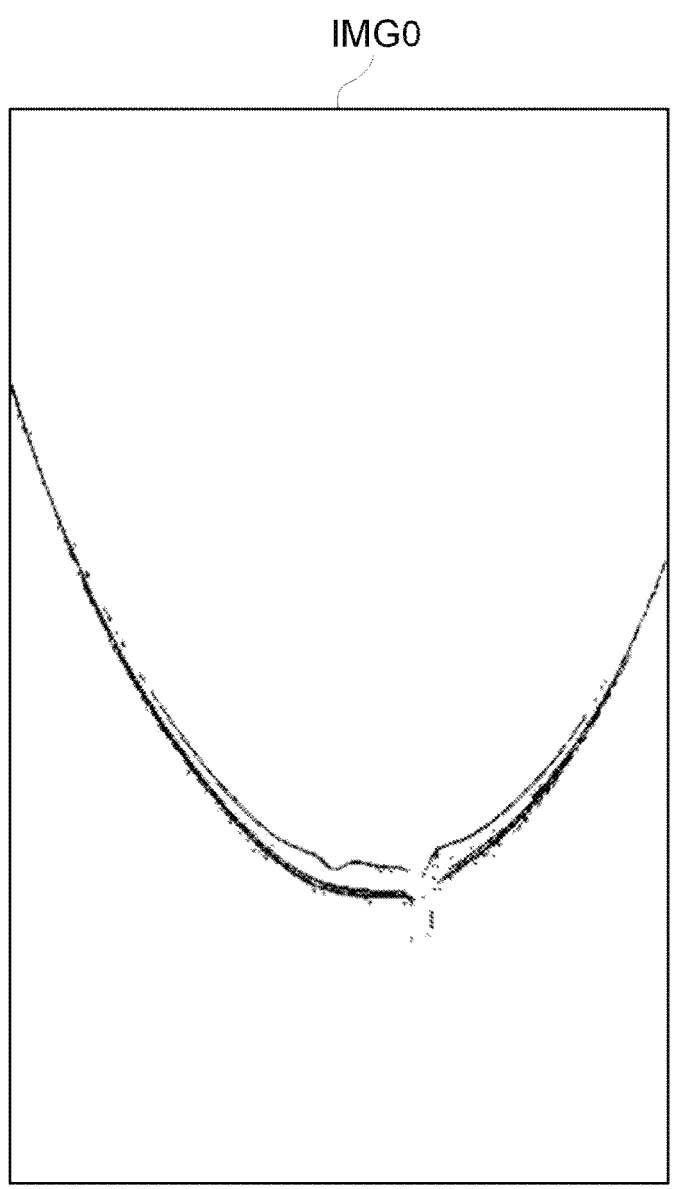
FIG. 6 is a schematic diagram for explaining processing performed by the ophthalmologic apparatus according to a comparative example of the embodiments.

FIGS. 5 and 6 show diagrams of comparative examples of the embodiments. FIG. 5 schematically shows the path of the measurement light incident on the subject's eye E. FIG. 6 shows an example of the tomographic image obtained by scanning with the measurement light incident on the subject's eye E through the path shown in FIG. 5.

The measurement light deflected by the optical scanner 42, for example, is incident on the pupil of the subject's eye E, which is a scan center position, at various incident angles, as shown in FIG. 5. The measurement light incident on the subject's eye E is projected toward each part in the eye around the scan center position Cs set at the center of the pupil, for example.

An A-scan image is formed from the interference data obtained using the measurement light LS1 in FIG. 5, an A-scan image is formed from the interference data obtained using the measurement light LS2, and an A-scan image is formed from the interference data obtained using the measurement light LS3. The tomographic image IMG0 of the fundus shown in FIG. 6 is formed by arranging the plurality of A-scan images thus formed.

In this way, the A scan directions vary within the scan angle range centered on the scan center position Cs, and the shape of the site is deformed in the tomographic images in which the obtained plurality of A scan images are arranged in the horizontal direction. The wider the angle of view is, the greater the difference from the actual shape becomes.

Further, morphology information representing the morphology of the subject's eye E can be obtained from the positions of arbitrary pixels in the tomographic image. Examples of the morphology information include an intraocular distance (including a distance between layer regions), an area of region, a volume of region, a perimeter of region, a direction of site with reference to a reference position, an angle of site with reference to a reference direction, and a curvature radius of site.

For example, the intraocular distance as the morphology information can be obtained by measuring a distance between arbitrary two points in the tomographic image. In this case, the distance between the two points can be specified using the number of pixels in the tomographic image, and can be measured by multiplying the specified number of pixels by the pixel size specific to the apparatus. At this time, the same pixel size is adopted for all pixels in the tomographic image. However, as described above, the scan directions are different with the scan center position Cs as the center. Thereby, the pixel size in the horizontal direction of the tomographic image differs depending on the depth position in the scan direction. For example, in case that the depth range is 2.5 millimeters, when the same pixel size is adopted for all pixels in the tomographic image, there is a difference of about 13% in the scan length of the B-scan between the upper portion and the lower portion of the tomographic image, and when the depth range is 10 millimeters, there is a difference of about 50%.

Therefore, the data processor 230 according to the embodiments performs coordinate transformation on the pixel positions in the acquired OCT image or the scan positions in the scan data. Hereinafter, the intraocular distance will be described as an example of the morphology information representing the morphology of the subject's eye E.

Such the data processor 230 includes a position specifying unit 231, a position transforming unit 232, an interpolator 233, and an intraocular distance calculator 234.
(Position Specifying Unit)

The position specifying unit 231 is configured to specify a transformation position along a traveling direction of the measurement light passing through the scan center position Cs, the transformation position corresponding to a pixel position in the acquired OCT image (or the scan position in the scan data). In some embodiments, the position specifying unit 231 uses the eyeball parameter 212A for performing processing for specifying the transformation position.

Figure 7:
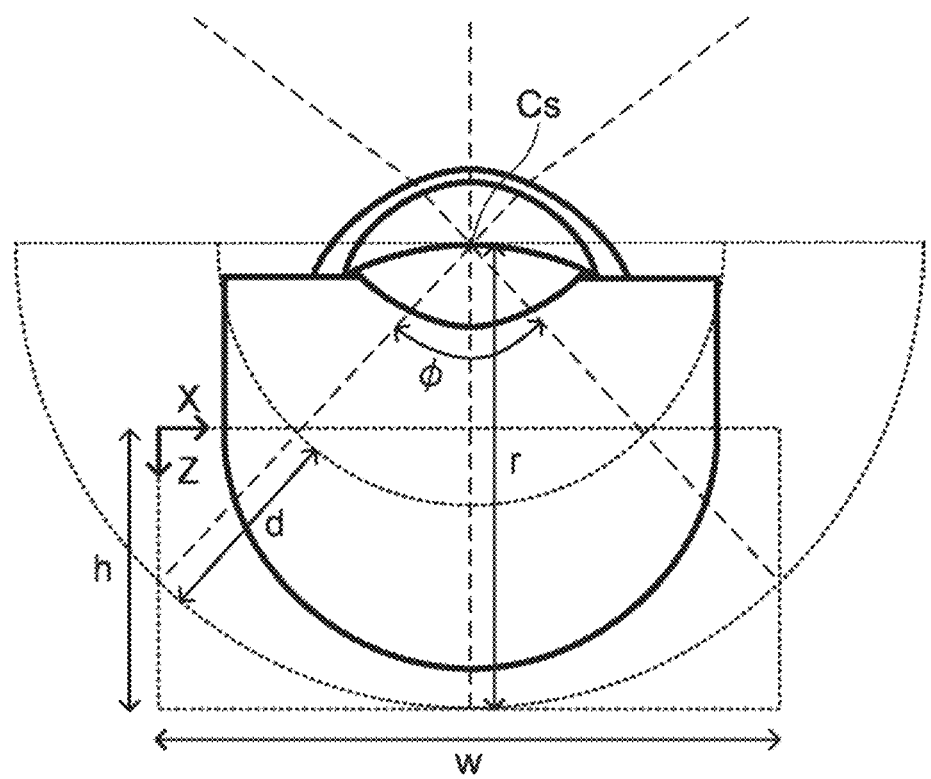
FIG. 7 is a schematic diagram for explaining processing performed by the ophthalmologic apparatus according to the embodiments.

FIG. 7 shows a diagram describing the operation of the position specifying unit 231 according to the embodiments. In FIG. 7, parts similarly configured to those in FIG. 5 are denoted by the same reference numerals, and the description thereof is omitted unless it is necessary.

Here, the scan angle is φ, the scan radius is r, the depth range in which OCT measurement can be performed d, the length of the tomographic image in the depth direction is h, and the lateral length of the tomographic image is w. The scan angle φ corresponds to the deflection angle of the measurement light LS around the scan center position Cs. The scan radius r corresponds to the distance from the scan center position Cs to a zero optical path length position where the measurement optical path length and the reference optical path length are substantially equal. The depth range d is a value (known) specific to the apparatus, the value being uniquely determined by the optical design of the apparatus.

The position specifying unit 231 specifies the transformation position (X, Z) in a second coordinate system from the pixel position (x, z) in a first coordinate system. The first coordinate system is a coordinate system having the origin at the upper left coordinate position in the OCT image (B-scan image). The first coordinate system is defined by an x coordinate axis having the B-scan direction as the x direction and a z coordinate axis, which is orthogonal to the x coordinate axis, having the A-scan direction as the z direction. The pixel position (x, z) in the OCT image is defined in the first coordinate system. The second coordinate system is defined a Z coordinate axis (for example, second axis) and a X coordinate axis (for example, first axis). The Z coordinate axis has the traveling direction of the measurement light LS having the scan angle of 0 degrees with respect to the measurement optical axis passing through a predetermined site (for example, fovea) in the fundus Ef, as the Z direction. The X coordinate axis has the B-scan direction orthogonal to the Z coordinate axis at the predetermined site, as the X direction. In the second coordinate system, a predetermined Z position is set as the origin of the Z coordinate axis so that the position of the scan radius r becomes the deepest portion in the measurement optical axis passing through the predetermined site (for example, the fovea). Further, a predetermined X position in the measurement optical axis passing through the predetermined site (for example, the fovea) is set as the origin of the X coordinate axis so as to have a predetermined depth direction length d as described below. The transformation position (X, Z) is defined in the second coordinate system. The transformation position (X, Z) corresponds to the pixel position (x, z), and is a position along the traveling direction of the measurement light LS passing through the scan center position Cs (A-scan direction).

For the OCT image, the position specifying unit 231 specifies the transformation position (X, Z) based on the scan radius r of the A-scan direction, the scan angle φ, the depth range d in which the OCT measurement can be performed, and the pixel position (x, z). The position specifying unit 231 can specify at least one of the X component of the transformation position (component of the first axis direction) and the Z component of the transformation position (component of the second axis direction).

For the OCT image (tomographic image) in which the number of A-scan lines is N (N is a natural number), the transformation position (X, Z), which corresponds to the pixel position (x, z) in the n-th (n is a natural number) A-scan line, is specified as shown in Equations (1) and (2).

[Equation 1]

$$X = \frac{w}{2} + (r - d + z) \times \sin\left(\frac{\phi}{N} \times n - \frac{\phi}{2}\right) \quad (1)$$

[Equation 2]

$$Z = (r - d + z) \times \cos\left(\frac{\phi}{N} \times n - \frac{\phi}{2}\right) - (r - d) \times \cos\frac{\phi}{2} \quad (2)$$

Here, the length h in the depth direction of the OCT image, the length w in the horizontal direction of the OCT image, and the x component of the pixel position are expressed by Equations (3) to (5).

[Equation 3]

$$h = r - (r-d) \times \cos\frac{\phi}{2} \quad (3)$$

[Equation 4]

$$w = 2r \times \sin\frac{\phi}{2} \quad (4)$$

[Equation 5]

$$x = n \quad (5)$$

In Equations (1) and (2), the x coordinate of the pixel position is expressed by Equation (5). Thus, the position specifying unit 231 can specify the transformation position (X, Z) from the pixel position (x, z), based on the scan radius r, the scan angle φ, and the depth range d.

In some embodiments, for the scan data, the position specifying unit 231 can specify the transformation position (X, Z) based on the scan radius r in the A-scan direction, the scan angle φ, the depth range d in which the OCT measurement can be performed, and the scan position, in the same way as above.

In some embodiments, the scan radius r is specified by analyzing the detection result of the interference light LC obtained using the OCT optical system 8. This allows to specify the transformation position (X, Z) that more accurately reflects the eyeball optical characteristics of subject's eye E.

In some embodiments, the position specifying unit 231 specifies the scan angle φ by performing ray trace processing on the measurement light LS based on the corneal shape information of the subject's eye E. Examples of the corneal shape information include a corneal curvature radius (curvature radius of an anterior surface of cornea, curvature radius of a posterior surface of cornea) and corneal thickness. This allows to specify the transformation position (X, Z) that more accurately reflects the eyeball optical characteristics of subject's eye E.

(Position Transforming Unit)

The position transforming unit 232 transforms the pixel position (x, z) in the OCT image into the transformation position (X, Z) specified by the position specifying unit 231. In some embodiments, for each of all pixel positions in the OCT image, the position specifying unit 231 specifies the transformation position and the position transforming unit 232 transforms the pixel position into the transformation position.

Figure 8:
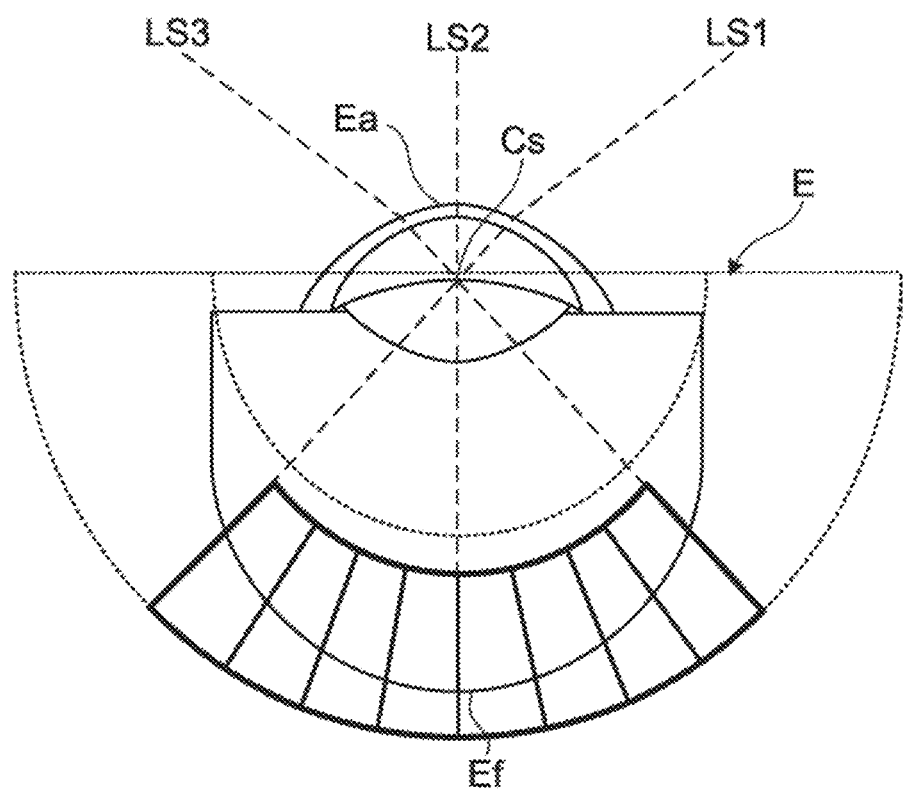
FIG. 8 is a schematic diagram for explaining processing performed by the ophthalmologic apparatus according to the embodiments.
Figure 9:
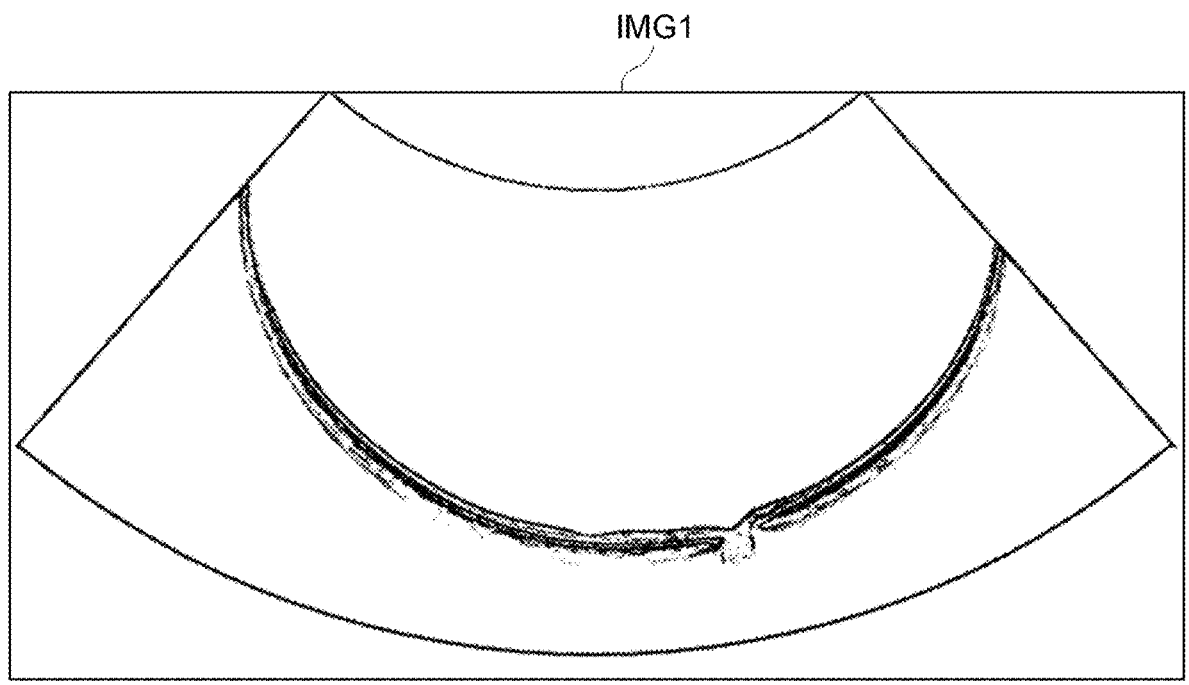
FIG. 9 is a schematic diagram for explaining processing performed by the ophthalmologic apparatus according to the embodiments.

This allows to arrange the A-scan images, which are acquired by performing A-scan, in the A-scan direction as shown in FIG. 8. Therefore, even if the angle of view is wide as in the tomographic image IMG1 shown in FIG. 9, the tomographic image in which the shape of the predetermined site is similar to the actual shape can be obtained.

(Interpolator)

The interpolator 233 interpolates pixels between the transformation positions. For example, intervals between the A-scan images adjacent to each other in which the pixel positions have been transformed into the transformation position varies depending on the distance from the scan center position Cs. The interpolator 233 interpolates pixel(s) between the A-scan images using a pixel in the A-scan images adjacent to each other according to the depth position in the A-scan image. As interpolation processing on pixels performed by the interpolator 233, a known method such as a nearest neighbor method, a bilinear interpolation method, or a bicubic interpolation method can be adopted. In some embodiments, the interpolator 233 interpolates pixels between the A-scan images adjacent to each other according to the distance from the scan center position Cs. For example, the interpolator 233 interpolates pixels between the A-scan images adjacent to each other by changing interpolation processing method according to the distance from the scan center position Cs.

In some embodiments, for the scan position in the scan data, the scan data is interpolated, in the same way as above.

(Intraocular Distance Calculator)

The intraocular distance calculator 234 calculates an intraocular distance of the subject's eye E based on the image OCT image in which the pixel position has been transformed into the transformation position by the position transforming unit 232.

The intraocular distance calculator 234 obtains the intraocular distance between predetermined sites in the subject's eye E based on the OCT image transformed by the position transforming unit 232. For example, the intraocular distance calculator 234 specifies the predetermined sites in the eye by analyzing the transformed OCT image, and obtains the intraocular distance described above based on the distance between the specified sites. The distance between the two points can be specified using the number of pixels in the tomographic image, and can be measured by multiplying the specified number of pixels by the pixel size specific to the apparatus. At this time, the same pixel size is adopted for all pixels in the tomographic image.

Examples of the intraocular distance between the predetermined sites include a distance between designated sites (tissue, layer region), an axial length, a distance from a scan center position of the measurement light, which is set at the center of the pupil, or the like, to a retina. In case that the axial length is obtained as the intraocular distance, the intraocular distance calculator 234 obtains the axial length based on a distance from a site corresponding to a corneal apex to a site corresponding to the retina.

In some embodiments, the intraocular distance calculator 234 calculates an intraocular distance of the subject's eye, in the same way as above, based on the scan data in which the scan position has been transformed into the transformation position by the position transforming unit 232.

The data processor 230 that functions as above includes, for example, a processor described above, a RAM, a ROM, a hard disk drive, a circuit board, and the like. In a storage device such as the hard disk drive, a computer program for causing the processor to execute the functions described above is stored in advance.

(User Interface)

The user interface 240 includes the display unit 240A and an operation unit 240B. The display unit 240A includes the aforementioned display device of the arithmetic control unit 200 and the display apparatus 3. The operation unit 240B includes the aforementioned operation device of the arithmetic control unit 200. The operation unit 240B may include various types of buttons and keys provided on the case of the ophthalmologic apparatus 1 or the outside. For example, when the fundus camera unit 2 has a case similar to that of the conventional fundus camera, the operation unit 240B may include a joy stick, an operation panel, and the like provided to the case. Besides, the display unit 240A may include various types of display devices such as a touch panel and the like arranged on the case of the fundus camera unit 2.

Note that the display unit 240A and the operation unit 240B need not necessarily be formed as separate devices. For example, a device like a touch panel, which has a display function integrated with an operation function, can be used. In such cases, the operation unit 240B includes the touch panel and a computer program. The content of operation performed on the operation unit 240B is fed to the controller 210 in the morphology of an electrical signal. Moreover, operations and inputs of information may be performed by using a graphical user interface (GUI) displayed on the display unit 240A and the operation unit 240B.

The optical system in the path from the interference optical system included in the OCT unit 100 to the objective lens 22, or these optical systems and the image forming unit 220 is an example of the "acquisition unit" according to the embodiments that acquires a plurality of A-scan images or a plurality of A-scan data using OCT.

[Operation]

The operation of the ophthalmologic apparatus 1 according to the embodiments will be described.

Figure 10:
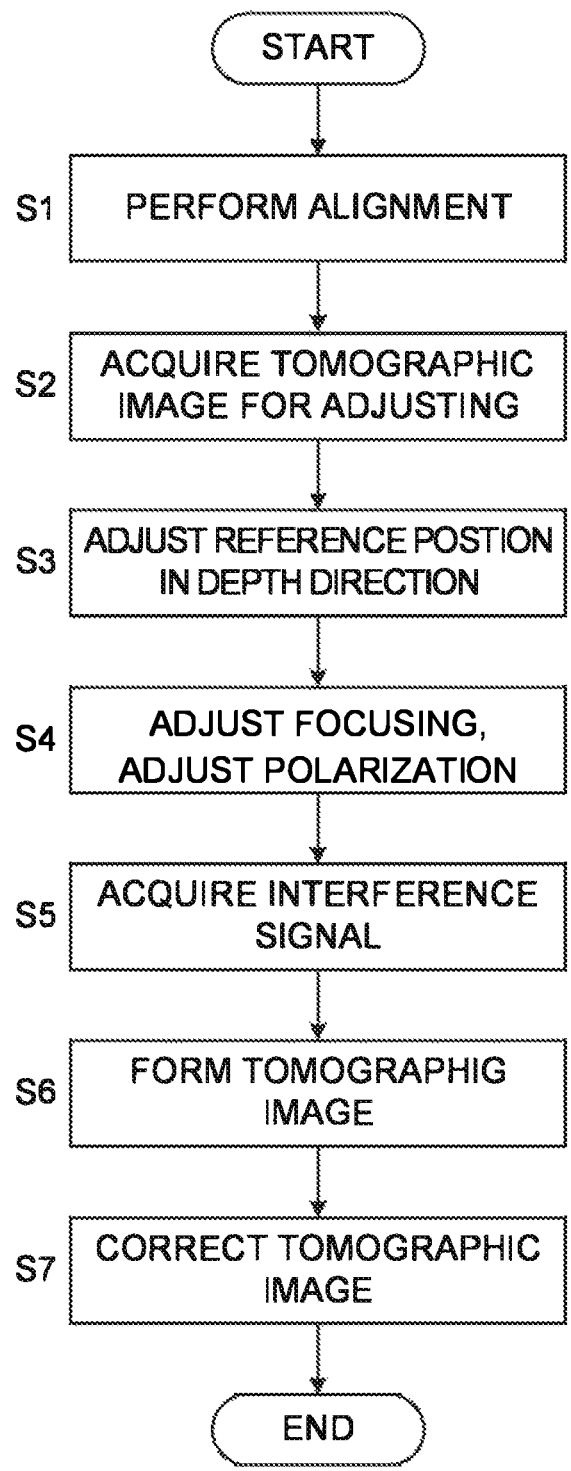
FIG. 10 is a schematic diagram illustrating an example of an operation of the ophthalmologic apparatus according to the embodiments.
Figure 11:
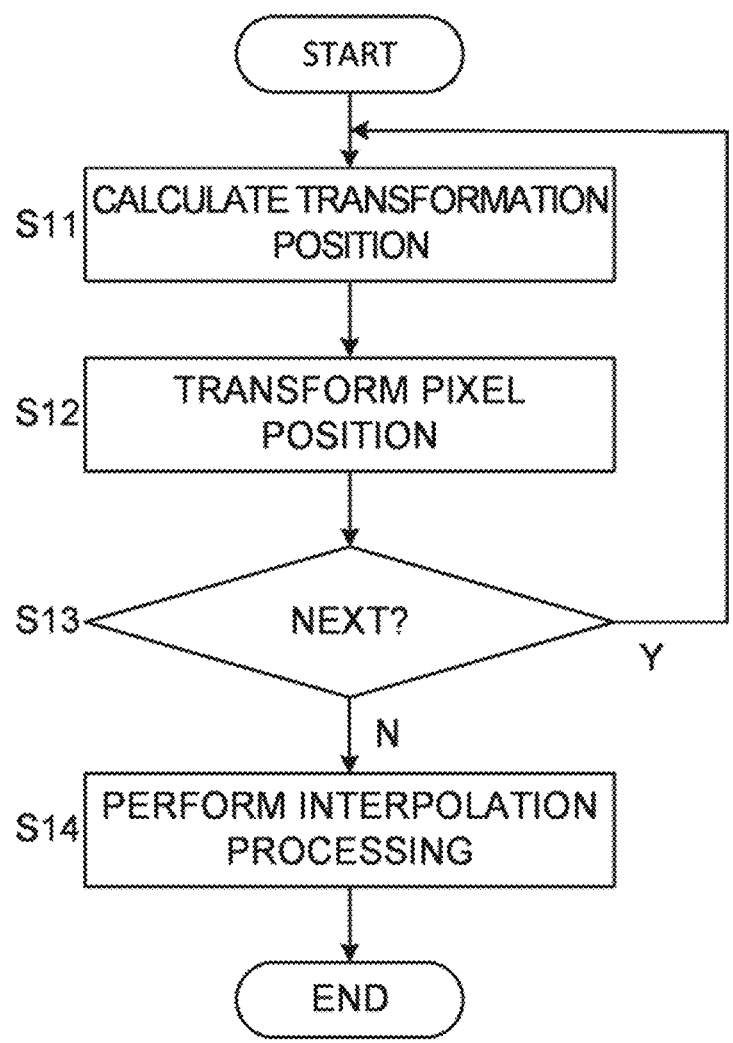
FIG. 11 is a schematic diagram illustrating an example of an operation of the ophthalmologic apparatus according to the embodiments.

FIG. 10 and FIG. 11 show an example of the operation of the ophthalmologic apparatus 1 according to the embodiments. FIG. 10 and FIG. 11 shows flowcharts of the example of the operation of the ophthalmologic apparatus 1 according to the embodiments. FIG. 11 shows a flowchart of an example of the operation of step S7 in FIG. 10. The storage unit 212 stores computer programs for realizing the processing shown in FIG. 10 and FIG. 11. The main controller 211 operates according to the computer programs, and thereby the main controller 211 performs the processing shown in FIG. 10 and FIG. 11.

(S1: Perform Alignment)

The main controller 211 performs alignment.

That is, the main controller 211 controls the alignment optical system 50 to project the alignment indicator onto the subject's eye E. At this time, a fixation target generated by the LCD 39 is also projected onto the subject's eye E. The main controller 211 controls the movement mechanism 150 based on the movement amount of the optical system to relatively to move the optical system with respect to the subject's eye E by the movement amount. The movement amount is specified based on the receiving light image obtained using the image sensor 35, for example. The main controller 211 repeatedly executes this processing.

In some embodiments, the alignment rough adjustment and the alignment fine adjustment are performed after the alignment in step S1 is completed.

(S2: Acquire Tomographic Image for Adjustment)

The main controller 211 controls the LCD 39 to display the fixation target for OCT measurement at a predetermined position on the LCD 39. The main controller 211 can display the fixation target at a display position on the LCD 39 corresponding to a position of an optical axis of the optical axis on the fundus Ef.

Subsequently, the main controller 211 controls the OCT unit 100 to perform OCT provisional measurement, and to acquire a tomographic image for adjustment for adjusting the reference position of the measurement range in the depth direction. Specifically, the main controller 211 controls the optical scanner 42 to deflect the measurement light LS generated based on the light L0 emitted from the light source unit 101 and to scan a predetermined site (for example, fundus) of the subject's eye E with the deflected measurement light LS. The detection result of the interference light obtained by scanning with the measurement light LS is sent to the image forming unit 220 after being sampled in synchronization with the clock KC. The image forming unit 220 forms the tomographic image (OCT image) of the subject's eye E from the obtained interference signal.

(S3: Adjust Reference Position in Depth Direction)

Subsequently, the main controller 211 adjusts the reference position of the measurement range in the depth direction (z direction).

For example, the main controller 211 controls the data processor 230 to specify a predetermined site (for example, sclera) in the tomographic image obtained in step S2, and sets a position separated by a predetermined distance in the depth direction from the specified position of the predetermined site as the reference position of the measurement range. The main controller 211 controls at least one of the optical path length changing units 41 and 114 according to the reference position. Alternatively, a predetermined position determined in advance so that the optical path lengths of the measurement light LS and the reference light LR substantially coincide may be set as the reference position of the measurement range.

(S4: Adjust Focusing, Adjust Polarization)

Next, the main controller 211 perform control of adjusting focusing and of adjusting polarization.

For example, the main controller 211 controls the OCT unit 100 to perform OCT measurement, after controlling the focusing driver 43A to move the OCT focusing lens 43 by a predetermined distance. The main controller 211 controls the data processor 230 to determine the focus state of the measurement light LS based on the detection result of the interference light acquired by the OCT measurement, as described above. When it is determined that the focus state is not appropriate based on the determination result of the data processor 230, the main controller 211 controls the focusing driver 43A again and repeats this until it is determined that the focus state of the measurement light LS is appropriate.

Further, for example, the main controller 211 controls the OCT unit 100 to perform OCT measurement after controlling at least one of the polarization controllers 103 and 118 to change the polarization state of at least one of the light L0 and the measurement light LS by a predetermined amount. And then, the main controller 211 controls the image forming unit 220 to form the OCT image on the basis of the acquired detection result of the interference light. The main controller 211 controls the data processor 230 to determine the image quality of the OCT image acquired by the OCT measurement, as described above. When it is determined that the polarization state is not appropriate based on the determination result of the data processor 230, the main controller 211 controls the polarization controllers 103 and 118 again and repeats this until it is determined that the polarization state of the measurement light LS is appropriate.

(S5: Acquire Interference Signal)

Subsequently, the main controller 211 controls the OCT unit 100 to perform OCT measurement. The detection result of the interference light acquired by the OCT measurement is sampled by the DAQ 130 and is stored as the interference signal in the storage unit 212 or the like.

(S6: Form Tomographic Image)

Next, the main controller 211 controls the image forming unit 220 to form the data set group of the A-scan image data of the subject's eye E based on the interference signal acquired in step S5. The image forming unit 220 forms the tomographic image as shown in FIG. 6, by arranging the formed A-scan images in the B-scan direction.

(S7: Correct Tomographic Image)

The main controller 211 corrects the tomographic image, which is formed in step S6, as described above using the eyeball parameter 212A stored in the storage unit 212. This allows to acquire the tomographic image in which the A-scan images are arranged in the A-scan direction.

Figure 12:
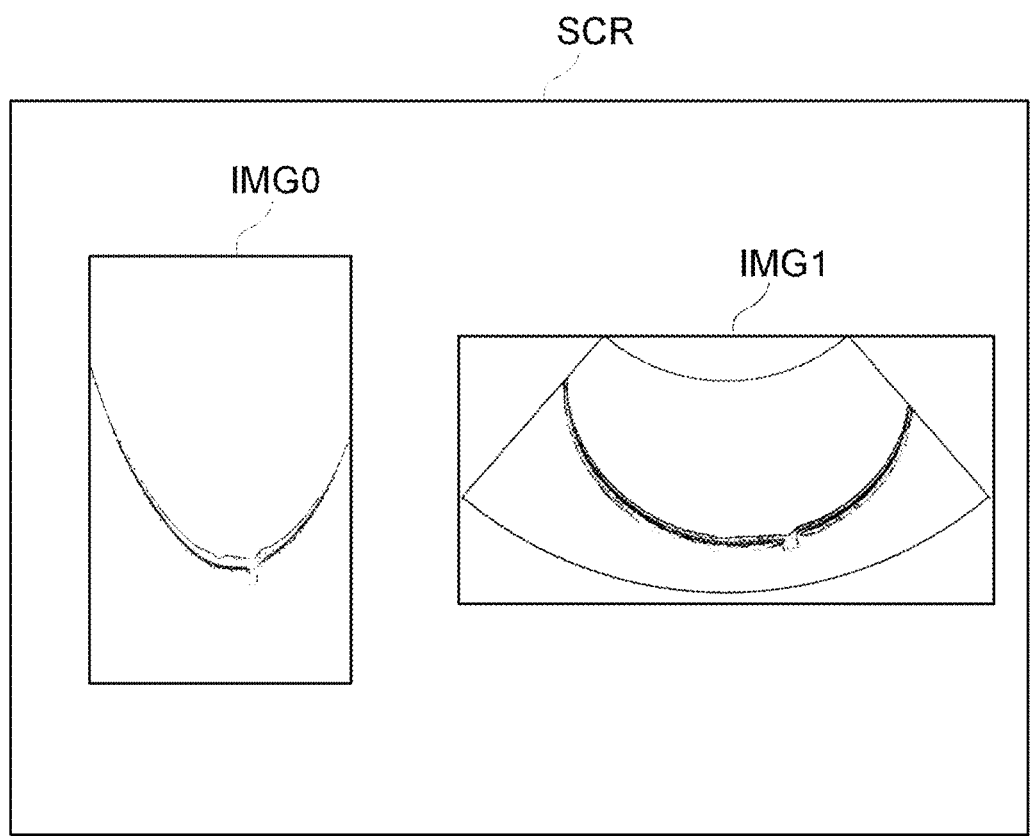
FIG. 12 is a schematic diagram for explaining processing performed by the ophthalmologic apparatus according to the embodiments.

For example, the main controller 211 controls the display unit 240A to display the newly generated tomographic image (for example, the tomographic image IMG1 shown in FIG. 9) and the tomographic image before correction (for example, the tomographic image IMG0 shown in FIG. 6) on the same screen SCR of the display unit 240A (FIG. 12). This allows to easily compare with the conventional tomographic images in which many imaging findings are accumulated, even if different morphologies are drawn in the conventional tomographic image by displaying the corrected tomographic image.

In some embodiments, the tomographic image before correction is displayed according to the measurement site. For example, when displaying a tomographic image or the like in the vicinity of the macula where the change in morphology is small before and after correction, the tomographic image before correction may be intentionally displayed.

This terminates the operation of the ophthalmologic apparatus 1 (END).

In step S7 in FIG. 10, processing as shown in FIG. 11 is performed.

(S11: Calculate Transformation Position)

In step S7, the main controller 211 controls the position specifying unit 231 to specify the transformation position corresponding to the pixel position in the tomographic image formed in step S6. The position specifying unit 231 specifies the transformation position corresponding to the pixel position in the tomographic image, as described above.

(S12: Transform Pixel Position)

Subsequently, the main controller 211 controls the position transforming unit 232 to transform the pixel position in the tomographic image into the transformation position calculated in step S11.

(S13: Next?)

The main controller 211 determine whether or not the next pixel position should be transformed.

When it is determined that the next pixel position should be transformed (S13: Y), the operation of the ophthalmologic apparatus proceeds to step S11. When it is determined that the next pixel position should not be transformed (S13: N), the operation of the ophthalmologic apparatus proceeds to step S14.

Through steps S11 to S13, for each pixel position of the tomographic image, specifying the transformation position and transforming to the specified transformation position are performed.

(S14: Perform Interpolation Processing)

When it is determined that the next pixel position should not be transformed in step S13 (S13: N), the main controller 211 controls the interpolator 233 to interpolate the pixels between the A-scan images adjacent to each other, A-scan images having been transformed into the transformation positions in step S12.

This terminates the processing of step S7 in FIG. 10 (END).

<Modification Example>

In the embodiments described above, the case has been described in which the two-dimensional OCT image (or the two-dimensional scan data) is corrected. However, the configuration according to the embodiments is not limited thereto. The ophthalmologic apparatus according to the embodiments can correct three-dimensional OCT data (or the three-dimensional scan data), as in the embodiments described above. Hereinafter, an ophthalmologic apparatus according to a modification example of the embodiments will be described focusing on differences from the embodiments.

The configuration of the ophthalmologic apparatus according to the modification example of the embodiments is similar to the configuration of the ophthalmologic apparatus 1 according to the embodiments. Therefore, the description thereof will be omitted.

The data processor according to the present modification example performs processing for specifying the transformation position in the three-dimensional space, or the like.

The position specifying unit 231 according to the present modification example specifies the transformation position along the traveling direction of the measurement light passing through the scan center position Cs, the transformation position corresponding to the pixel position in the acquired OCT image (or the scan position in the scan data). In some embodiments, the position specifying unit 231 specifies the transformation position using the eyeball parameter 212A.

Figure 13:
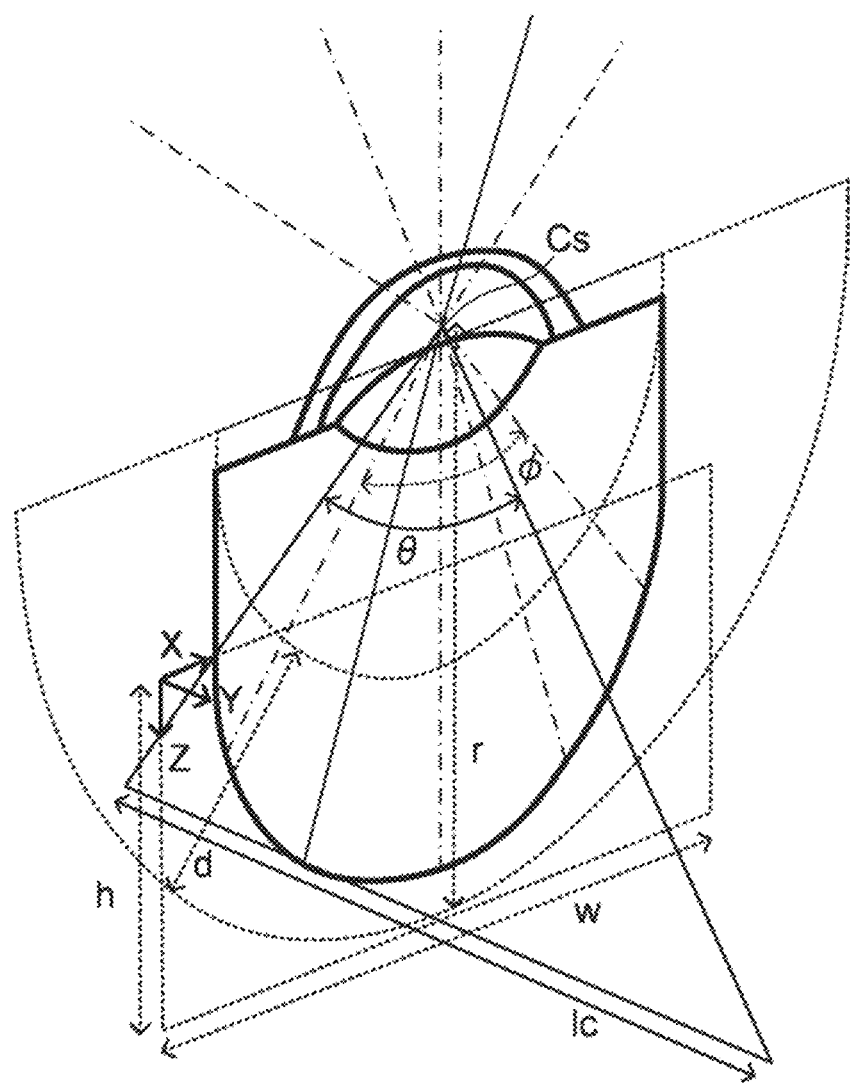
FIG. 13 is a schematic diagram for explaining processing performed by the ophthalmologic apparatus according to a modification example of the embodiments.

FIG. 13 shows a diagram describing the operation of the position specifying unit 231 according to the present modification example. In FIG. 13, parts similarly configured to those in FIG. 7 are denoted by the same reference numerals, and the description thereof is omitted unless it is necessary.

In FIG. 13, a Y plane is defined in addition to the X plane and the Z plane in FIG. 7. In addition to the parameters shown in FIG. 7, the central angle in the C-scan direction is θ, and the length in the C-scan direction is lc.

The position specifying unit 231 specifies the transformation position (X, Y, Z) in a fourth coordinate system from the pixel position (x, y, z) in a third coordinate system. The third coordinate system is a coordinate system having the origin at the upper left coordinate position in the three-dimensional OCT image. The third coordinate system is defined by the x coordinate axis having the B-scan direction as the x direction, a y coordinate axis, which is orthogonal to the x coordinate axis, having the C-scan direction as the y direction, and the z coordinate axis, which is orthogonal to both of the x coordinate axis and they coordinate axis, having the A-scan direction as the z direction. The pixel position (x, y, z) in the OCT image is defined in the third coordinate system. The fourth coordinate system is defined the Z coordinate axis, the X coordinate axis, and a Y coordinate axis. The Z coordinate axis has the traveling direction of the measurement light LS having the scan angle of 0 degrees with respect to the measurement optical axis passing through a predetermined site (for example, fovea) in the fundus Ef, as the Z direction. The X coordinate axis has the B-scan direction orthogonal to the Z coordinate axis at the predetermined site, as the X direction. The Y coordinate axis has the C-scan direction orthogonal to the Z coordinate axis at the predetermined site, as the Y direction. In the fourth coordinate system, a predetermined Z position is set as the origin of the Z coordinate axis so that the position of the scan radius r becomes the deepest portion in the measurement optical axis passing through the predetermined site (for example, the fovea). Further, a predetermined X position and Y position in the measurement optical axis passing through the predetermined site (for example, the fovea) are set as the origin of the X coordinate axis and the Y coordinate axis so as to have a predetermined depth direction length d as described below. The transformation position (X, Y, Z) is defined in the fourth coordinate system. The transformation position (X, Y, Z) corresponds to the pixel position (x, y, z), and is a position along the traveling direction of the measurement light LS passing through the scan center position Cs (A-scan direction).

The position specifying unit 231 can specify at least one of the X component, the Y component, and the Z component of the transformation position.

For the OCT image (tomographic image) in which the number of A-scan lines is N (N is a natural number) and the number of B-scan lines is M (M is a natural number), the transformation position (X, Y, Z), which corresponds to the pixel position (x, y, z) in the n-th (n is a natural number) A-scan line of the m-th (m is a natural number) B-scan line, is specified as shown in Equations (6) to (8).

[Equation 6]

$$X = \frac{w}{2} + \frac{(r-d+z) \times \tan\left(\frac{\phi}{N} \times n - \frac{\phi}{2}\right)}{\sqrt{\tan^2\left(\frac{\phi}{N} \times n - \frac{\phi}{2}\right) + \tan^2\left(\frac{\theta}{M} \times m - \frac{\theta}{2}\right) + 1}} \quad (6)$$

[Equation 7]

$$Y = \frac{lc}{2} + \frac{(r-d+z) \times \tan\left(\frac{\theta}{M} \times m - \frac{\theta}{2}\right)}{\sqrt{\tan^2\left(\frac{\phi}{N} \times n - \frac{\phi}{2}\right) + \tan^2\left(\frac{\theta}{M} \times m - \frac{\theta}{2}\right) + 1}} \quad (7)$$

[Equation 8]

$$Z = \frac{(r-d+z)}{\sqrt{\tan^2\left(\frac{\phi}{N} \times n - \frac{\phi}{2}\right) + \tan^2\left(\frac{\theta}{M} \times m - \frac{\theta}{2}\right) + 1}} - (r-h) \quad (8)$$

Here, the x component and the y component of the pixel position are expressed by Equations (9) to (13) from the length h in the depth direction, the length w in the B-scan direction, and the length lc in the C-scan direction of the three-dimensional OCT image.

[Equation 9]

$$h = r - (r-d) \times \cos\frac{\phi}{2} \quad (9)$$

[Equation 10]

$$w = 2r \times \sin\frac{\phi}{2} \quad (10)$$

[Equation 11]

$$lc = 2r \times \sin\frac{\theta}{2} \quad (11)$$

[Equation 12]

$$x = n \quad (12)$$

[Equation 13]

$$y = m \quad (13)$$

In Equations (6) to (8), the x coordinate and the y coordinate of the pixel position are expressed by Equations (12) and Equation (13). Thus, the position specifying unit 231 can specify the transformation position (X, Y, Z) from the pixel position (x, y, z), based on the scan radius r, the scan angle φ, and the depth range d.

In some embodiments, for the scan data, the position specifying unit 231 can specify the transformation position (X, Y, Z), in the same way as above.

The position transforming unit 232 according to the present modification example transforms the pixel position (x, y, z) in the OCT image into the transformation position (X, Y, Z) specified by the position specifying unit 231. In some embodiments, for each of all pixel positions in the OCT image, the position specifying unit 231 specifies the transformation position and the position transforming unit 232 transforms the pixel position into the transformation position.

In the embodiments described above, the case where the tomographic image is corrected in the ophthalmologic apparatus including the OCT unit 100, and the like has been described. However, the configuration according to the embodiments is not limited thereto. For example, the ophthalmologic information processing apparatus, which realizes the function of the data processor 230 shown in FIG. 4, may correct the tomographic image for the acquired OCT image (or the scan data), as described above. In this case, the OCT image (or the scan data) is acquired by an external OCT apparatus (ophthalmologic apparatus).

In some embodiments, a program for causing a computer to execute the ophthalmologic information processing described above is provided. Such a program can be stored in any computer-readable recording medium (for example, a non-transitory computer readable medium). Examples of the recording medium include a semiconductor memory, an optical disk, a magneto-optical disk (CD-ROM, DVD-RAM, DVD-ROM, MO, etc.), a magnetic storage medium (hard disk, floppy (registered trade mark) disk, ZIP, etc.), and the like. The computer program may be transmitted and received through a network such as the Internet, LAN, etc.

[Effects]

Hereinafter, the ophthalmologic information processing apparatus, the ophthalmologic apparatus, the ophthalmologic information processing method, and the program according to the embodiments will be described.

An ophthalmologic information processing apparatus (for example, the apparatus including the data processor 230) according to some embodiments corrects an image (OCT image) of a subject's eye (E) formed by arranging a plurality of A-scan images acquired by scanning inside the subject's eye with measurement light (LS) deflected around a scan center position (Cs). The ophthalmologic information processing apparatus includes a specifying unit (position specifying unit 231) and a transforming unit (position transforming unit 232). The specifying unit is configured to specify a transformation position along a traveling direction of the measurement light passing through the scan center position, the transformation position corresponding to a pixel position in the image. The transforming unit is configured to transform the pixel position into the transformation position specified by the specifying unit.

According to such a configuration, each of the plurality of A-scan images can be arranged in the A-scan direction. This allows to acquire an image in which the actual morphology is drawn even if the angle of view becomes wide. Therefore, the actual shape or the like of the predetermined site in the eye can be specified.

Some embodiments includes a calculator (intraocular distance calculator 234) configured to calculate morphology information representing morphology of the subject's eye, based on the image in which the pixel position is transformed into the transformation position by the transforming unit.

According to such a configuration, even when the angle of view becomes wide, the morphology information representing the morphology of the subject's eye can be accurately obtained.

In some embodiments, the morphology information includes an intraocular distance.

According to such a configuration, even when the angle of view becomes wide, the intraocular distance between arbitrary sites can be accurately obtained.

In some embodiments, the specifying unit is configured to specify at least one of a component of a first axis direction (for example, the X axis direction) of the transformation position and a component of a second axis direction (for example, the Z axis direction) of the transformation position in a predetermined coordinate system, the second axis direction intersecting the first axis direction, based on a scan radius (r) in the traveling direction, a scan angle ($\varphi$), a depth range (d) that can be measured using optical coherence tomography, and the pixel position.

According to such a configuration, the transformation position can be specified by performing simple processing using the scan radius, the scan angle, the depth range and the pixel position, and each of the plurality of A-scan images can be arranged in the A-scan direction, based on the specified transformation position.

An ophthalmologic information processing apparatus (for example, the apparatus including the data processor 230) corrects two-dimensional or three-dimensional scan data of a subject's eye (E) formed by arranging a plurality of A-scan data acquired by scanning inside the subject's eye with measurement light (LS) deflected around a scan center position (Cs). The ophthalmologic information processing apparatus includes a specifying unit (position specifying unit 231) and a transforming unit (position transforming unit 232). The specifying unit is configured to specify a transformation position along a traveling direction of the measurement light passing through the scan center position, the transformation position corresponding to a scan position in the scan data. The transforming unit is configured to transform the scan position into the transformation position specified by the specifying unit.

According to such a configuration, each of the plurality of A-scan data can be arranged in the A-scan direction. This allows to acquire scan data representing the actual morphology even if the angle of view becomes wide. Therefore, the actual shape or the like of the predetermined site in the eye can be specified.

Some embodiments includes an image forming unit (220) configured to form an image (OCT image) of the subject's eye based on the scan data in which the scan position is transformed into the transformation position by the transforming unit.

According to such a configuration, even when the angle of view becomes wide, the image in which the actual morphology is drawn can be acquired.

Some embodiments includes a calculator (intraocular distance calculator 234) configured to calculate morphology information representing morphology of the subject's eye, based on the scan data in which the scan position is transformed into the transformation position by the transforming unit.

According to such a configuration, even when the angle of view becomes wide, the morphology information representing the morphology of the subject's eye can be accurately obtained.

In some embodiments, the morphology information includes an intraocular distance.

According to such a configuration, even when the angle of view becomes wide, the intraocular distance between arbitrary sites can be accurately obtained.

In some embodiments, the specifying unit is configured to specify at least one of a component of a first axis direction (for example the X axis direction) of the transformation position and a component of a second axis direction (for example, the Z axis direction) of the transformation position in a predetermined coordinate system, the second axis direction intersecting the first axis direction, based on a scan radius (r) in the traveling direction, a scan angle ($\varphi$), a depth range (d) that can be measured using optical coherence tomography, and the scan position.

According to such a configuration, the transformation position can be specified by performing simple processing using the scan radius, the scan angle, the depth range and the pixel position, and each of the plurality of A-scan images can be arranged in the A-scan direction, based on the specified transformation position.

In some embodiments, the specifying unit is configured to specify the scan angle by performing ray trace processing on the measurement light based on corneal shape information of the subject's eye.

According to such a configuration, the transformation position that more accurately reflects the eyeball optical characteristics of subject' eye can be specified.

Some embodiments includes an interpolator (233) configured to interpolate pixels or scan data between the transformation positions.

According to such a configuration, the image or the scan data representing morphology similar to the actual morphology, even when the intervals between the transformation positions in adjacent A scan images or A scan data varies depending on the distance from the scan center position.

In some embodiments, the specifying unit is configured to specify the transformation position based on a parameter representing optical characteristics of the subject's eye.

According to such a configuration, the transformation position that more accurately reflects the eyeball optical characteristics of subject' eye can be specified.

An ophthalmologic apparatus (1) includes an acquisition unit (the optical system in the path from the interference optical system included in the OCT unit 100 to the objective lens 22, or these optical systems and the image forming unit 220) configured to acquire the plurality of A-scan images or the plurality of A-scan data using optical coherence tomography; and the ophthalmologic information processing apparatus of any one of the above.

According to such a configuration, each of the plurality of A-scan images or the plurality of A-scan data can be arranged in the A-scan direction. This allows to acquire an image or scan data representing the actual morphology even if the angle of view becomes wide. Therefore, the actual shape or the like of the predetermined site in the eye can be specified.

An ophthalmologic information processing method according to some embodiments corrects an image (OCT image) of a subject's eye (E) formed by arranging a plurality of A-scan images acquired by scanning inside the subject's eye with measurement light (LS) deflected around a scan center position (Cs). The ophthalmologic information processing method includes an specifying step and a transformation step. The specifying step is performed to specify a transformation position along a traveling direction of the measurement light passing through the scan center position, the transformation position corresponding to a pixel position in the image. The transforming step is performed to transform the pixel position into the transformation position specified in the specifying step.

According to such a method, each of the plurality of A-scan images can be arranged in the A-scan direction. This allows to acquire an image in which the actual morphology is drawn even if the angle of view becomes wide. Therefore, the actual shape or the like of the predetermined site in the eye can be specified.

Some embodiments include a calculation step of calculating morphology information representing morphology of the subject's eye, based on the image in which the pixel position is transformed into the transformation position in the transforming step.

According to such a method, even when the angle of view becomes wide, the morphology information representing the morphology of the subject's eye can be accurately obtained.

An ophthalmologic information processing method according to some embodiments corrects two-dimensional or three-dimensional scan data of a subject's eye (E) formed by arranging a plurality of A-scan data acquired by scanning inside the subject's eye with measurement light (LS) deflected around a scan center position (Cs). The ophthalmologic information processing method includes an specifying step and a transformation step. The specifying step is performed to specify a transformation position along a traveling direction of the measurement light passing through the scan center position, the transformation position corresponding to a scan position in the scan data. The transforming step is performed to transform the scan position into the transformation position specified in the specifying step.

According to such a method, each of the plurality of A-scan data can be arranged in the A-scan direction. This allows to acquire scan data representing the actual morphology even if the angle of view becomes wide. Therefore, the actual shape or the like of the predetermined site in the eye can be specified.

Some embodiments include an image forming step of forming an image (OCT image) of the subject's eye based on the scan data in which the scan position is transformed into the transformation position in the transforming step.

According to such a method, even when the angle of view becomes wide, the image in which the actual morphology is drawn can be acquired.

Some embodiments includes a calculation step of calculating morphology information representing morphology of the subject's eye, based on the scan data in which the scan position is transformed into the transformation position in the transforming step.

According to such a method, even when the angle of view becomes wide, the morphology information representing the morphology of the subject's eye can be accurately obtained.

In some embodiments, the morphology information includes an intraocular distance.

According to such a method, even when the angle of view becomes wide, the intraocular distance between arbitrary sites can be accurately obtained.

Some embodiments include an interpolation step of interpolating pixels or scan data between the transformation positions.

According to such a method, the image or the scan data representing morphology similar to the actual morphology, even when the intervals between the transformation positions in adjacent A scan images or A scan data varies depending on the distance from the scan center position.

In some embodiments, the specifying step is performed to specify the transformation position based on a parameter representing optical characteristics of the subject's eye.

According to such a method, the transformation position that more accurately reflects the eyeball optical characteristics of subject' eye can be specified.

A program according to some embodiments causes a computer to execute each step of the ophthalmologic information processing method of any one of the above.

According to such a program, even when the angle of view becomes wide, the image in which the actual morphology is drawn or the scan data representing the actual morphology can be acquired Therefore, the actual shape or the like of the predetermined site in the eye can be specified.

<Others>

The above-described some embodiments or the modification examples thereof are merely examples for carrying out the present invention. Those who intend to implement the present invention can apply any modification, omission, addition, or the like within the scope of the gist of the present invention.

The invention has been described in detail with particular reference to preferred embodiments thereof and examples, but it will be understood that variations and modifications can be effected within the spirit and scope of the invention covered by the claims which may include the phrase "at least one of A, B and C" as an alternative expression that means one or more of A, B and C may be used, contrary to the holding in *Superguide v. DIRECTV,* 69 USPQ2d 1865 (Fed. Cir. 2004).

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

The invention claimed is:

1. An ophthalmologic information processing apparatus for correcting an image of a subject's eye formed by arranging a plurality of A-scan images acquired by scanning inside the subject's eye with measurement light deflected around a scan center position, the ophthalmologic information processing apparatus comprising:

processing circuitry configured to specify a transformation position along a traveling direction of the measurement light passing through the scan center position, the transformation position corresponding to a pixel position in the image;

the processing circuitry further configured to transform the pixel position into the transformation position; and the processing circuitry further configured to interpolate pixels between the transformation positions, and to interpolate the pixels between the A-scan images adjacent to each other according to a distance from the scan center position.

2. The ophthalmologic information processing apparatus of claim 1, further comprising a calculator configured to calculate morphology information representing morphology of the subject's eye, based on the image in which the pixel position is transformed into the transformation position.

3. The ophthalmologic information processing apparatus of claim 2, wherein
the morphology information includes an intraocular distance.

4. The ophthalmologic information processing apparatus of claim 1, wherein
the processing circuitry is configured to specify at least one of a component of a first axis direction of the transformation position and a component of a second axis direction of the transformation position in a predetermined coordinate system, the second axis direction intersecting the first axis direction, based on a scan radius in the traveling direction, a scan angle, a depth range that can be measured using optical coherence tomography, and the pixel position.

5. An ophthalmologic information processing apparatus for correcting two-dimensional or three-dimensional scan data of a subject's eye formed by arranging a plurality of A-scan data acquired by scanning inside the subject's eye with measurement light deflected around a scan center position, the ophthalmologic information processing apparatus comprising:
processing circuitry configured to specify a transformation position along a traveling direction of the measurement light passing through the scan center position, the transformation position corresponding to a scan position in the scan data;
the processing circuitry further configured to transform the scan position into the transformation position; and
the processing circuitry further configured to interpolate scan data between the transformation positions, and to interpolate the scan data between the A-scan images adjacent to each other according to a distance from the scan center position.

6. The ophthalmologic information processing apparatus of claim 5, further comprising
an image forming circuit configured to form an image of the subject's eye based on the scan data in which the scan position is transformed into the transformation position.

7. The ophthalmologic information processing apparatus of claim 5, further comprising
a calculator configured to calculate morphology information representing morphology of the subject's eye, based on the scan data in which the scan position is transformed into the transformation position.

8. The ophthalmologic information processing apparatus of claim 7, wherein
the morphology information includes an intraocular distance.

9. The ophthalmologic information processing apparatus of claim 5, wherein
the processing circuitry is configured to specify at least one of a component of a first axis direction of the transformation position and a component of a second axis direction of the transformation position in a predetermined coordinate system, the second axis direction intersecting the first axis direction, based on a scan radius in the traveling direction, a scan angle, a depth range that can be measured using optical coherence tomography, and the scan position.

10. The ophthalmologic information processing apparatus of claim 4, wherein
the processing circuitry is configured to specify the scan angle by performing ray trace processing on the measurement light based on corneal shape information of the subject's eye.

11. The ophthalmologic information processing apparatus of claim 1, wherein
the processing circuitry is configured to specify the transformation position based on a parameter representing optical characteristics of the subject's eye.

12. An ophthalmologic apparatus, comprising:
an acquisition unit including circuitry and a sensor configured to acquire the plurality of A-scan images or the plurality of A-scan data using optical coherence tomography; and
an ophthalmologic information processing apparatus for correcting an image of a subject's eye formed by arranging a plurality of A-scan images acquired by scanning inside the subject's eye with measurement light deflected around a scan center position, the ophthalmologic information processing apparatus including processing circuitry configured to specify a transformation position along a traveling direction of the measurement light passing through the scan center position, the transformation position corresponding to a pixel position in the image, the processing circuitry further configured to transform the pixel position into the transformation position, and the processing circuitry further configured to interpolate pixels between the transformation positions, and to interpolate the pixels between the A-scan images adjacent to each other according to a distance from the scan center position.

13. An ophthalmologic information processing method of correcting an image of a subject's eye formed by arranging a plurality of A-scan images acquired by scanning inside the subject's eye with measurement light deflected around a scan center position, the ophthalmologic information processing method comprising:
specifying a transformation position along a traveling direction of the measurement light passing through the scan center position, the transformation position corresponding to a pixel position in the image;
transforming the pixel position into the transformation position, and
interpolating pixels between the transformation positions to interpolate pixels between the A-scan images adjacent to each other according to the distance from the scan center position.

14. The ophthalmologic information processing method of claim 13, further comprising
calculating morphology information representing morphology of the subject's eye, based on the image in which the pixel position is transformed into the transformation position.

15. The ophthalmologic information processing method of claim 14, wherein
the morphology information includes an intraocular distance.

16. The ophthalmologic information processing method of claim 13, further comprising
specifying the transformation position based on a parameter representing optical characteristics of the subject's eye.

17. A non-transitory computer readable recording medium storing a program of causing a computer to execute steps of correcting an image of a subject's eye formed by arranging a plurality of A-scan images acquired by scanning inside the subject's eye with measurement light deflected around a scan center position, the steps executed by the computer comprising:
- specifying a transformation position along a traveling direction of the measurement light passing through the scan center position, the transformation position corresponding to a pixel position in the image;
- transforming the pixel position into the transformation position, and
- interpolating pixels between the transformation positions to interpolate pixels between the A-scan images adjacent to each other according to the distance from the scan center position.

* * * * *